(12) United States Patent
Hellerqvist et al.

(10) Patent No.: US 8,609,614 B2
(45) Date of Patent: Dec. 17, 2013

(54) GBS TOXIN RECEPTOR COMPOSITIONS AND METHODS OF USE

(75) Inventors: Carl G. Hellerqvist, Nashville, TN (US); Changlin Fu, Chesterfield, MO (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/022,357

(22) Filed: Feb. 7, 2011

(65) Prior Publication Data

US 2011/0217316 A1 Sep. 8, 2011

Related U.S. Application Data

(60) Continuation-in-part of application No. 12/142,060, filed on Sep. 19, 2008, now abandoned, and a continuation-in-part of application No. 12/331,067, filed on Dec. 9, 2008, now abandoned, which is a continuation-in-part of application No. 09/776,865, filed on Feb. 2, 2001, now abandoned, and a continuation-in-part of application No. 12/142,060, which is a division of application No. 10/823,506, filed on Apr. 12, 2004, now Pat. No. 7,410,640, which is a division of application No. 09/359,167, filed on Jul. 21, 1999, now Pat. No. 6,803,448.

(60) Provisional application No. 60/179,870, filed on Feb. 2, 2000, provisional application No. 60/093,843, filed on Jul. 22, 1998.

(51) Int. Cl.
*A61K 38/17* (2006.01)
*A61K 38/03* (2006.01)
*C07K 14/435* (2006.01)

(52) U.S. Cl.
USPC .............................. 514/12; 514/15; 530/350

(58) Field of Classification Search
None
See application file for complete search history.

(56) References Cited

U.S. PATENT DOCUMENTS

| | | | |
|---|---|---|---|
| 3,842,067 A | 10/1974 | Sarantakis | |
| 3,862,925 A | 1/1975 | Sarantakis et al. | |
| 3,972,859 A | 8/1976 | Fujino et al. | |
| 4,105,602 A | 8/1978 | Colescott et al. | |
| 4,242,326 A | 12/1980 | Sugawara et al. | |
| 4,284,537 A | 8/1981 | Beachey | |
| 4,399,216 A | 8/1983 | Axel et al. | |
| 4,579,821 A | 4/1986 | Palmiter et al. | |
| 4,619,828 A | 10/1986 | Gordon | |
| 4,673,574 A | 6/1987 | Anderson | |
| 4,740,461 A | 4/1988 | Kaufman | |
| 4,761,283 A | 8/1988 | Anderson | |
| 4,789,735 A | 12/1988 | Frank et al. | |
| 4,816,397 A | 3/1989 | Boss et al. | |
| 4,912,040 A | 3/1990 | Kaufman et al. | |
| 4,946,778 A | 8/1990 | Ladner et al. | |
| 4,959,455 A | 9/1990 | Clark et al. | |
| 5,010,062 A | 4/1991 | Hellergvist | |
| 5,811,403 A | 9/1998 | Hellerqvist | |
| 5,858,991 A | 1/1999 | Hellerqvist et al. | |
| 5,939,396 A | 8/1999 | Hellerqvist | |
| 5,981,508 A | 11/1999 | Hellerqvist et al. | |
| 6,803,448 B1 | 10/2004 | Hellerqvist | |
| 7,410,640 B2 | 8/2008 | Hellerqvist | |
| 2002/0061846 A1 | 5/2002 | Hellerqvist | |
| 2003/0129176 A1* | 7/2003 | Jones et al. ................... | 424/94.1 |
| 2009/0221804 A1 | 9/2009 | Hellerqvist et al. | |
| 2010/0076184 A1 | 3/2010 | Hellerqvist | |

FOREIGN PATENT DOCUMENTS

| | | |
|---|---|---|
| EP | 0173494 | 3/1986 |
| EP | 0206852 | 12/1986 |
| EP | 0239400 | 9/1987 |
| EP | 0245045 | 11/1987 |
| EP | 0325199 | 7/1989 |
| EP | 0445280 | 4/1996 |
| WO | WO-9014430 | 11/1990 |
| WO | WO-9104048 | 4/1991 |
| WO | WO-9110424 | 7/1991 |
| WO | WO-9420085 | 9/1994 |
| WO | WO-9741844 | 11/1997 |
| WO | WO-9814603 | 4/1998 |
| WO | WO-9832448 | 7/1998 |
| WO | WO-9832452 | 7/1998 |
| WO | WO-9832453 | 7/1998 |
| WO | WO-9840487 | 9/1998 |
| WO | WO-0005375 | 2/2000 |

OTHER PUBLICATIONS

Ross, Atherosclerosis—an inflammatory disease. N. Engl. J. Med 340:115-126, 1999.*

Sequence alignment provided in an Office Action for U.S. Appl. No. 12/142,060, filed Jun. 19, 2008 Feb. 16, 2011.

(Continued)

*Primary Examiner* — Ruixiang Li

(74) *Attorney, Agent, or Firm* — Kilpatrick Townsend & Stockton LLP

(57) ABSTRACT

Methods are provided for preventing or attenuating pathoangiogenic conditions by administering at least one GBS toxin receptor polypeptide or at least one immunogenic fragment thereof. Also provided are a composition that includes a GBS toxin receptor polypeptide and a method for making such a composition. In another embodiment of the invention, immunized animals also receive GBS toxin, immunocompatible antibodies to the GBS toxin receptor, and/or expanded autologous T cells to the GBS toxin receptor. Also included in this invention are methods of identifying additional GBS toxin receptors.

10 Claims, 2 Drawing Sheets

(56) References Cited

OTHER PUBLICATIONS

Chong, et al., "Molecular cloning of the cDNA encoding a human renal sodium phosphate transport protein and its assignment to", Genomics 18 1993, 355-359.
Ngo, et al., "Computational complexity, protein structure predictions, an the Levinthal Paradox, in the Protein Folding Problem and Tertiary Structure Prediction", Merz et al. (ed.), Birkhauser, Boston, MA 1994, 433 and 492-495.
Sambrook, et al., "Molecular Cloning of the cDNA encoding a human renal sodium phosphate transport protein and its assignment to chromosome 6p21.3-p23", Genomics 1993, 18:355-359.
Wallace, et al., "The relative contribution of electrostatic interactions to stabilization of collagen fibrils", Biopolymers May-Jun. 1990, 29(6-7): 1015-26.
Wallace, et al., "Oligonucleotide probes for the screening of recombinant DNA libraries", Methods in Enzymology, 1987, 432-442.
Remington's Pharmeceutical Science 19th Ed., Mock Publishing Co., Easton, PA , 1995, table of contents.
Sigma Catalogue, 1992, p. 1419.
Alberts, et al., Molecular Biology of the Cell, 2nd Edition, 1989, pp. 564-570.
Anderson, "Antibody responses to Haemophilus influenzae type b and diphtheria toxin induced by conjugates of oligosaccharides of the type b capsule with the nontoxic protein CRM197," Infect. Immun., 1983, 39:233-238.
Arceci, "The potential for antitumor vaccination in acute myelogenous leukemia." Journal of Molecular Medicine, 1998, 76:80-93.
Benton, et al., "Screening lambdagt recombinant clones by hybridization to single plaques in situ." Science, 1977, 196:180.
Bergman, et al., "Two regulatory elements for immunoglobulin kappa light chain gene expression." Proc. Natl. Acad. Science USA, 1984, 81:7041-7045.
Bessler, "Specific antibodies elicited by antigen covalently linked to a synthetic adjuvant." Immunobiol., 1985, 170:239-244.
Bocchia, et al., "Antitumor vaccination: where we stand." Haematologica, 2000, 85:1172-1206.
Bodey, et al., "Failure of cancer vaccines: the significant limitations of this approach to immunotherapy." Anticancer Research, 2000, 20:2665-2676.
Boon, "Toward a genetic analysis of tumor rejection antigens." Advances in Cancer Research, 1992, 58:177-210.
Boshart, et al., "A very strong enhancer is located upstream of an immediate early gene of human cytomegalovirus." Cell, 1985, 41:521-530.
Braspenning, et al., "Secretion of heterologous proteins from Schizosaccharomyces pombe using the homologous leader sequence of pho1+ acid phosphatase." Biochem. Biophys. Res. Commun., 1998, 245:166-171.
Brem, et al., "Analysis of experimental antiangiogenic therapy." J. Ped. Surg., 1993, 28:445-450.
Chou, et al., "Prediction of the secondary structure of proteins from their amino acid sequence" Advances in Enzymology, 1978, 47:45-148.
Chou, et al., "Prediction of beta-turns." Biophys. J., 1979, 26:367-383.
Chu, et al., "Further studies on the immunogenicity of Haemophilus influenzae type b and pneumococcal type 6A polysaccharide-protein conjugates." Infect. Immun., 1983, 40:245-256.
Cox, et al., "Identification of a peptide recognized by five melanoma-specific human cytotoxic T cell lines." Science, 1994, 264:716-719.
Dennis, "Off by a Whisker," Cancer News Feature, Nature, Aug. 7, 2006, 442:739-741.
Denoto, et al., "Human growth hormone DNA sequence and mRNA structure: possible alternative splicing." Nuc. Acids Research, 1981, 9:3719-3730.
Devore, et al., "A Phase I Study of the Anti-Neovascularization Drug CM-101," Proceedings of the Annual Meeting of the American Society of Clinical Oncology, 1995, p. 487.

Devore, et al., "Phase I Study of the Anti-neovascularization Drug CM-101," Clinical Cancer Research, 1997, 3:365-372.
Dijkema, et al., "Cloning and expression of the chromosomal immune interferon gene of the rat." EMBO J., 1985, 4:761.
Edwards, et al., "Capsular polysaccharide regulates neutrophil complement receptor interactions with type III group B streptococci." Infect. Immun., Jul. 1993, 61(7):2866-71.
Ezzell, "Cancer 'Vaccines': An Idea Whose Time Has Come?" Journal of NIH Research, 1995, 7:46-49.
Folkman, et al., "Angiogenic factors." Science, 1987, 235:442-447.
Fu, et al., "Identification of a novel membrane protein, HP59, with therapeutic potential as a target of tumor angiogenesis." Clin. Cancer Res., Dec. 2001, 7(12):4182-94.
Fu, et al., "Expressional Cloning of CM101 Receptor Gene from Mammalian Cells," Proceedings of the American Association of Cancer Research, Abstract No. 3677, 1999.
Fujiwara, et al., "Potential Role of the Slit/Robo Signal Pathway in Angiogenesis," Vascular Medicine, Vasc Med. 11(2):115-21, 2006.
Gao, et al.," Tumor vaccination that enhances antitumor T-cell responses does not inhibit the growth of established tumors even in combination with interleukin-12 treatment: the importance of inducing intratumoral T-cell migration." Journal of Immunotherapy, 2000, 23:643-653.
Gascuel, et al., "A simple method for predicting the secondary structure of globular proteins: implications and accuracy" CABIOS, 1988, 4:357-365.
Gearing, et al., "Expression Cloning of a Receptor for Human Granulocyte-Macrophage Colony-Stimulating Factor," The EMBO Journal, 1989, 8(12):3667-3676.
Geysen, et al., "Use of peptide synthesis to probe viral antigens for epitopes to a resolution of a single amino acid." Proc. Natl. Acad. Sci. USA, 1984, 81(13):3998-4002.
Ghose, et al., "Induction of polyclonal and monoclonal antibody responses to cholera toxin by the synthetic peptide approach." Molec. Immunol., 1988, 25:223-230.
Gillies, "A tissue-specific transcription enhancer element is located in the major intron of a rearranged immunoglobulin heavy chain gene." Cell, 1983, 33:717.
Gorman, et al., "The Rous sarcoma virus long terminal repeat is a strong promoter when introduced into a variety of eukaryotic cells by DNA-mediated transfection." Proc. Natl. Acad. Sci., 1982, 79:6777-6781.
Grant, et al.,"Improved RNA sequencing method to determine immunoglobulin mRNA sequence." Nuc. Acids Res., 1987, 15:5496.
Gura, "Systems for identifying new drugs are often faulty." Science, 1997, 278:1041-1042.
Harlow, et al., "Antibodies A Laboratory Manual," Cold Spring Harbor Press, 1989, pp. 141-241.
Hellerqvist, et al., "Modulation of interleukin-12 mRNA expression in leukocytes of cancer patients treated with CM101." Ann. NY Acad. Sci., Oct. 31, 1996, 795:346-348.
Hellerqvist, et al., "Anti-Tumor Effects of GBS Toxin are Caused by Induction of a Targeted Inflammatory Reaction," Angiogenesis: Molecular Biology, Clinical Aspects, Edited by Maragoudakis et al., Plenum Press, New York, 1994, pp. 265-269.
Hellerqvist, et al., "Antitumor Effects of GBS Toxin: A Polysaccharide Exotoxin From Group B β-Hemolytic Streptococcus," J. Cancer Res. Clin. Oncol., 1993, 120:63-70.
Hellerqvist, et al., "Molecular Basis for Group B β-Hemolytic Streptococcal Disease," Proc. Natl. Acad. Sci. USA, 1987, 84:51-55.
Hellerqvist, et al., "Preliminary Results of a Phase I Trial of CM101 in Cancer Patients," Cellular Biochemistry, 1995, Suppl. 19B, p. 26.
Hellerqvist, et al., "Molecular basis for group B beta-hemolytic streptococcal disease." Proc. Natl. Acad. Sci., 1987, 84:51-55.
Hellerqvist, et al., "Studies on Group B β-Hemolytic Streptococcus. I. Isolation and Partial Characterization of an Extracellular Toxin," Pediatr. Res., 1981, 15:892-898.
Henneke, et al., "Novel engagement of CD14 and multiple toll-like receptors by group B streptococci." J. Immunol., Dec. 15, 2001, 167(12):7069-7076.
Hillier, et al., "zr59d01.r1Soares NhHMPu S1 Homo Sapiens cDNA Clone 667681 5' Similar to Tr:G507415 G507415 Brain Specific

(56) References Cited

OTHER PUBLICATIONS

Na+-Dependent Inorganic Phosphate Cotransporter," Database EMBL—EMEST20 'Online!, Entry HS1173506, Acc. No. AA258513, Mar. 19, 1997.
Hoffman, et al., "Orthotopic metastatic mouse models for anticancer drug discovery and evaluation: a bridge to the clinic." Invest. New Drugs, 1999, 17(4):343-359.
Hopp, et al., "Prediction of protein antigenic determinants from amino acid sequences." Proc. Natl. Acad. Sci., 1981, 78:3824-3828.
Jacob, et al., "Priming immune response to cholera toxin induced by synthetic peptides." Eur. J. Immunol., 1986, 16:1057-1062.
Karplus, et al., "Prediction of chain flexibility in proteins." Naturwissenschaften, 1985, 72:212-213.
Kaufman, et al., "Construction of a modular dihydrofolate reductase cDNA gene: analysis of signals utilized for efficient expression." Mol. Cell. Biol., 1982, 2:1304-1319.
Kelland, "Of mice and men: values and liabilities of the athymic nude mouse model in anticancer drug development." Eur. J. Cancer, Apr. 2004, 40(6):827-836.
Kimball, et al., "Angiogenesis in pannus formation." Agents & Actions, 1991, 34:329-331.
Klipstein, et al., "Development of a vaccine of cross-linked heat-stable and heat-labile enterotoxins that protects against *Escherichia coli* producing either enterotoxin." Infect. Immun., 1982, 37:550-557.
Kovacs, et al., "Fibrogenic Cytokines and Connective Tissue Production," The FASEB Journal, 1994, 8:854-861.
Kusters, et al., "Analysis of an immunodominant region of infectious bronchitis virus." J. Immunol., 1989, 143:2692-2698.
Kusters, et al., "Improvement of the cloning linker of the bacterial expression vector pEX." Nuc. Acids Res., 1989, 17, 8007.
Lee, et al., "Increased vaccine-specific T cell frequency after peptide-based vaccination correlates with increased susceptibility to in vitro stimulation but does not lead to tumor regression." Journal of Immunology, 1999, 163:6292-6300.
Lepow, "Clinical trials of the Haemophilus influenzae type b capsular polysaccharide-diphtheria diphtheria toxoid conjugate vaccine." Pediat. Infect. Dis. J., 1987, 6:804-807.
Liles, et al., "Activation of protein kinase C induces rapid internalization and subsequent degradation of muscarinic acetylcholine receptors in neuroblastoma cells." J. Biol. Chem., 1986, 261:5307-5313.
Liu, et al., "Neuronal and glial apoptosis after traumatic spinal cord injury." J. Neuroscience, 1997, 17:5395-5406.
Loh, et al., "Molecular basis of a mouse strain-specific anti-hapten response." Cell, 1983, 33:85-93.
Maniatis, et al., "Regulation of inducible and tissue-specific gene expression." Science, 1987, 236:1237-1245.
Merrifield, "Solid Phase Peptide Synthesis. I. The Synthesis of a Tetrapeptide" J. Am. Chem. Soc., 1963, 85:2149-2154.
Mikayama, "Molecular Closing and Functional Expression of a cDNA Encoding Glycosylation-Inhibiting Factor," Proc. Natl. Acad. Sci. USA, 1993, 90:10056-10060.
Moriguchi, et al., "The effectiveness of active specific immunotherapy using interferon-gamma-gene-transduced tumor cells in a murine tumor model." Surg. Today, 1997, 27(6):571-573.
Nair, et al., "Regression of tumors in mice vaccinated with professional antigen-presenting presenting cells pulsed with tumor extracts." Int. J. Cancer, Mar. 17, 1997, 70(6):706-15.
Ni, et al., "Closing and Expression of a cDNA Encoding a Brain-Specific Na(+)- Dependent Inorganic Phosphate Cotransporter," Proc. Natl. Acad. Sci. U.S.A., 1994, 91:5607-5611.
Norrby, "Angiogenesis: New Aspects Relating to Its Initiation and Control," APMIS 1997, 105:417-437.
Novotny, et al., "A program for prediction of protein secondary structure from nucleotide sequence data: application to histocompatibility antigens." Nucleic Acids Research, 1984, 12:243-255.
Onofri, et al., "Localization of Vascular Endothelial Growth Factor (VEGF) Receptors in Normal and Adenomatous Pituitaries: Detection of a Non-Endothelial Function of Vegf in Pituitary Tumors," Journal of Endocrinology, Oct. 2006, 191:249-261.
Parker, et al., "A General Method to Prepare Synthetic Peptide Conjugates," in Modern Approaches to Vaccines, Cold Spring Harbor Laboratory, Cold Spring Harbor, NY, 1983:133-138.
Pearson, et al., "Improved tools for biological sequence comparison." Proc. Natl. Acad. Sci. USA, 1988, 85:24444-2448.
Peterson, et al., "Integrating pharmacology and in vivo cancer models in preclinical and clinical drug development." European Journal of Cancer, 2004, 40:837-844.
Polverini, "The Pathophysiology of Angiogenesis," Crit. Rev. Oral. Biol. Med., 1995, 6(3):230-247.
Posnett, et al., "A novel method for producing anti-peptide antibodies. Production of site-specific antibodies to the T cell antigen receptor beta-chain."J. Biol. Chem., 1988, 263:1719-1725.
Quinn, et al., "CM101, A Polysaccharide Antitumor Agent, Does Not Inhibit Wound Healing in Murine Models," J. Cancer Res. Clin. Oncol., 1995, 121:253-256.
Saijo, et al., "What are the reasons for negative phase Iii trials of molecular-targetbased drugs?" Cancer Sci., Oct. 2004, 95(10):772-776.
Sasada, et al., "Secretion of human EGF and IgE in mammalian cells by recombinant Dna techniques; use of a IL-2 leader sequence." Cell Struct. Funct., 1988, 13:129-141.
Sassone-Corsi, et al., "Transcriptional regulation by trans-acting factors" Trends Genet., 1986, 2:215-219.
Schuh, "Trials, tribulations, and trends in tumor modeling in mice." Toxicol. Pathol., Mar.-Apr. 2004, 32(Suppl. 1):53-66.
Shafer-Weaver, et al., "T cell tolerance to tumors and cancer immunotherapy." Adv. Exp. Med. Biol., 2007, 601:357-368.
Spitler, "Cancer vaccines: the interferon analogy." Cancer Biotherapy, 1995, 10:1-3.
Stanley, et al., "Construction of a new family of high efficiency bacterial expression vectors: identification of cDNA clones coding for human liver proteins." EMBOJ, 1984, 3:1429-1434.
Stewart, et al., "Solid Phase Peptide Synthesis," W.H. Freeman Co., San Francisco, 1963:1-26.
Subramani, et al., "Expression of the mouse dihydrofolate reductase complementary deoxyribonucleic acid in simian virus 40 vectors." Mol. Cell. Biol., 1981, 1:854-864.
Sundell, et al., "Isolation and identification of the group B streptococcal toxin CM101 from infants with sepsis." J. Pediatri., 2000, 137:338-344.
Thurman, et al., "Acute Inflammatory Changes in Subcutaneous Microtumors in the Ears of Mice Induced by Intravenous CM101 (GBS Toxin)," J. Cancer Res. Clin. Oncol., 1996, 122:549-553.
Voet, et al., "Biochemistry," John Wiley & Sons, Inc., 1990, pp. 126-128 and 228-234.
Voskoglou-Nomikos, et al., "inical predictive value of the in vitro cell line, human xenograft, and mouse allograft preclinical cancer models." Clin. Cancer Res., Sep. 15, 2003, 9:4227-4239.
Wamil, et al., "CM101 inhibits VEGF induced tumor neovascularization as determined by MRI and. RT-PCR" AACR Proceedings, 1997, 38:237.
Wamil, et al., Soluble E-Selectin in Cancer Patients as a Maker of the Therapeutic Efficacy of CM101, a Tumor-Inhibiting Anti-Neovascularization Agent, Elevated in Phase I Clinical Trial, J. Cancer Res. Clin. Oncol., 1997, 123:173-179.
Wang, et al., "T-cell-directed cancer vaccines: the melanoma model." Exp. Opin. Biol. Ther., 2001, 1(2):277-290.
Yu, et al., "Cancer vaccines: progress reveals new complexities." J. Clin. Invest., Aug. 2002, 110(3):289-94.
Yan, et al., "Functional studies on the anti-pathoangiogenic properties of CM101." Angiogenesis, 1998, 2:219-233.
Zaks, et al., "Immunization with a peptide epitope (p369-377) from HER-2/neu leads to peptide-specific cytotoxic T lymphocytes that fail to recognize HER-2/neu+ tumors." Cancer Research, 1998, 58:4902-4908.
Zurawski, et al., "Antibodies of restricted heterogeneity directed against the cardiac glycoside digoxin." J. Immunol., 1978, 121:122-129.

\* cited by examiner

SEQUENCE LISTING

<160> NUMBER OF SEQ ID NOS: 4

<210> SEQ ID NO 1
<211> LENGTH: 2930
<212> TYPE: DNA
<213> ORGANISM: Homo sapiens
<220> FEATURE:
<221> NAME/KEY: CDS
<222> LOCATION: (263)..(1870)

<400> SEQUENCE: 1

```
gttcggtcga agccctcccc ttaattatgt gcaattcaag tccccactgc ccgcccgcaa         60
gcccccactc atcctcgctg cgggcagggt ggccctgca  ctttacaagg gggtgcagga        120
gcgggagacg gtcgtccgaa caccggctcc ccggcatgcg tagaccggcg ggcggagcgg        180
gctcactttg cgccaatcct acgagaactc ccagaactcc gcttccctag tccaacccaa        240
gccagagttg cccacaccta ag atg gcg gcg ggg gcg atg aca ccg ccc cgc         292
                         Met Ala Ala Gly Ala Met Thr Pro Pro Arg
                          1               5                  10 ccg gtc cag cca gct cgg ccc ggg ggc ttc ggg ctg tcg ggc cgg cgc         340
Pro Val Gln Pro Ala Arg Pro Gly Gly Phe Gly Leu Ser Gly Arg Arg
             15                  20                  25 tcc ctt ctc tgc cag gtg gcg agt aca cct gct cac gta ggc gtc atg         388
Ser Leu Leu Cys Gln Val Ala Ser Thr Pro Ala His Val Gly Val Met
         30                  35                  40 agg tct ccg gtt cga gac ctg gcc cgg aac gat ggc gag gag agc acg         436
Arg Ser Pro Val Arg Asp Leu Ala Arg Asn Asp Gly Glu Glu Ser Thr
     45                  50                  55 gac cgc acg cct ctt cta ccg ggc gcc cca cgg gcc gaa gcc gct cca         484
Asp Arg Thr Pro Leu Leu Pro Gly Ala Pro Arg Ala Glu Ala Ala Pro
 60                  65                  70 gtg tgc tgc tct gct cgt tac aac tta gca att ttg gcc ttt ttt ggt         532
Val Cys Cys Ser Ala Arg Tyr Asn Leu Ala Ile Leu Ala Phe Phe Gly
 75                  80                  85                  90 ttc ttc att gtg tat gca tta cgt gtg aat ctg agt gtt gcg tta gtg         580
Phe Phe Ile Val Tyr Ala Leu Arg Val Asn Leu Ser Val Ala Leu Val
                 95                 100                 105 gat atg gta gat tca aat aca act tta gaa gat aat aga act tcc aag         628
Asp Met Val Asp Ser Asn Thr Thr Leu Glu Asp Asn Arg Thr Ser Lys
            110                 115                 120 gcg tgt cca gag cat tct gct ccc ata aaa gtt cat cat aat caa acg         676
Ala Cys Pro Glu His Ser Ala Pro Ile Lys Val His His Asn Gln Thr
        125                 130                 135 ggt aag aag tac caa tgg gat gca gaa act caa gga tgg att ctc ggt         724
Gly Lys Lys Tyr Gln Trp Asp Ala Glu Thr Gln Gly Trp Ile Leu Gly
    140                 145                 150 tcc ttt ttt tat ggc tac atc atc aca cag att cct gga gga tat gtt         772
Ser Phe Phe Tyr Gly Tyr Ile Ile Thr Gln Ile Pro Gly Gly Tyr Val
155                 160                 165                 170 gcc agc aaa ata ggg ggg aaa atg ctg cta gga ttt ggg atc ctt ggc         820
Ala Ser Lys Ile Gly Gly Lys Met Leu Leu Gly Phe Gly Ile Leu Gly
                175                 180                 185 act gct gtc ctc acc ctg ttc act ccc att gct gca gat tta gga gtt         868
Thr Ala Val Leu Thr Leu Phe Thr Pro Ile Ala Ala Asp Leu Gly Val
            190                 195                 200 gga cca ctc att gta ctc aga gca cta gaa gga cta gga gag ggt gtt         916
Gly Pro Leu Ile Val Leu Arg Ala Leu Glu Gly Leu Gly Glu Gly Val
        205                 210                 215 aca ttt cca gcc atg cat gcc atg tgg tct tct tgg gct ccc cct ctt         964
```

```
                                         -continued
Thr Phe Pro Ala Met His Ala Met Trp Ser Ser Trp Ala Pro Pro Leu
    220             225             230
gaa aga agc aaa ctt ctt agc att tcg tat gca gga gca cag ctt ggg    1012
Glu Arg Ser Lys Leu Leu Ser Ile Ser Tyr Ala Gly Ala Gln Leu Gly
235             240             245             250
aca gta att tct ctt cct ctt tct gga ata att tgc tac tat atg aat    1060
Thr Val Ile Ser Leu Pro Leu Ser Gly Ile Ile Cys Tyr Tyr Met Asn
                255             260             265
tgg act tat gtc ttc tac ttt ttt ggt act att gga ata ttt tgg ttt    1108
Trp Thr Tyr Val Phe Tyr Phe Phe Gly Thr Ile Gly Ile Phe Trp Phe
        270             275             280
ctt ttg tgg atc tgg tta gtt agt gac aca cca caa aaa cac aag aga    1156
Leu Leu Trp Ile Trp Leu Val Ser Asp Thr Pro Gln Lys His Lys Arg
            285             290             295
att tcc cat tat gaa aag gaa tac att ctt tca tca tta aga aat cag    1204
Ile Ser His Tyr Glu Lys Glu Tyr Ile Leu Ser Ser Leu Arg Asn Gln
        300             305             310
ctt tct tca cag aag tca gtg ccg tgg gta ccc att tta aaa tcc ctg    1252
Leu Ser Ser Gln Lys Ser Val Pro Trp Val Pro Ile Leu Lys Ser Leu
315             320             325             330
cca ctt tgg gct atc gta gtt gca cac ttt tct tac aac tgg act ttt    1300
Pro Leu Trp Ala Ile Val Val Ala His Phe Ser Tyr Asn Trp Thr Phe
                335             340             345
tat act tta ttg aca tta ttg cct act tat atg aag gag atc cta agg    1348
Tyr Thr Leu Leu Thr Leu Leu Pro Thr Tyr Met Lys Glu Ile Leu Arg
        350             355             360
ttc aat gtt caa gag aat ggg ttt tta tct tca ttg cct tat tta ggc    1396
Phe Asn Val Gln Glu Asn Gly Phe Leu Ser Ser Leu Pro Tyr Leu Gly
            365             370             375
tct tgg tta tgt atg atc ctg tct ggt caa gct gct gac aat tta agg    1444
Ser Trp Leu Cys Met Ile Leu Ser Gly Gln Ala Ala Asp Asn Leu Arg
380             385             390
gca aaa tgg aat ttt tca act tta tgt gtt cgc aga att ttt agc ctt    1492
Ala Lys Trp Asn Phe Ser Thr Leu Cys Val Arg Arg Ile Phe Ser Leu
395             400             405             410
ata gga atg att gga cct gca gta ttc ctg gta gct gct ggc ttc att    1540
Ile Gly Met Ile Gly Pro Ala Val Phe Leu Val Ala Ala Gly Phe Ile
                415             420             425
ggc tgt gat tat tct ttg gcc gtt gct ttc cta act ata tca aca aca    1588
Gly Cys Asp Tyr Ser Leu Ala Val Ala Phe Leu Thr Ile Ser Thr Thr
        430             435             440
ctg gga ggc ttt tgc tct tct gga ttt agc atc aac cat ctg gat att    1636
Leu Gly Gly Phe Cys Ser Ser Gly Phe Ser Ile Asn His Leu Asp Ile
            445             450             455
gct cct tcg tat gct ggt atc ctc ctg ggc atc aca aat aca ttt gcc    1684
Ala Pro Ser Tyr Ala Gly Ile Leu Leu Gly Ile Thr Asn Thr Phe Ala
460             465             470
act att cca gga atg gtt ggg ccc gtc att gct aaa agt ctg acc cct    1732
Thr Ile Pro Gly Met Val Gly Pro Val Ile Ala Lys Ser Leu Thr Pro
475             480             485             490
gat aac act gtt gga gaa tgg caa acc gtg ttc tat att gct gct gct    1780
Asp Asn Thr Val Gly Glu Trp Gln Thr Val Phe Tyr Ile Ala Ala Ala
                495             500             505
att aat gtt ttt ggt gcc att ttc ttt aca cta ttc gcc aaa ggt gaa    1828
Ile Asn Val Phe Gly Ala Ile Phe Phe Thr Leu Phe Ala Lys Gly Glu
        510             515             520
gta caa aac tgg gct ctc aat gat cac cat gga cac aga cac               1870
Val Gln Asn Trp Ala Leu Asn Asp His His Gly His Arg His
            525             530             535 tgaaggaacc aataaataat cctgcctcta ttaatgtatt tttatttatc atgtaacctc    1930
```

```
aaagtgcctt ctgtattgtg taagcattct atgtcttttt ttaattgtac ttgtattaga    1990
tttttaaggc ctataatcat gaaatatcac tagttgccag aataataaaa tgaactgtgt    2050
ttaattatga ataatatgta agctaggact tctactttag gttcacatac ctgcctgcta    2110
gtcgggcaac atgaagtagg acagttctgt tgatttttta gggccatact aaagggaatg    2170
agctgaaaca gacctcctga tacctttgct taattaaact agatgataat tctcaggtac    2230
tgataaacac ctgttgttgt tcactttcct cataaaaatt gtcagctctc tctgacactt    2290
agacctcaaa ctttagcatc tctgtggagc tgccatccac tgtataattt cgcctggcaa    2350
ctggactgag gggagtgtgc ccaggcagct gccaagcact ccctccctgg cttcagggtc    2410
agagtgccca gcgtttatca gaggcagcat ccaagcccag agccagtgtc gactcttcgg    2470
ctggtgcctt tcctctgagg ggctatcaat gtgtagataa agccctgagt aggcaagagc    2530
agtgagatcc actgctatgg tcttgataca tcctcaaact ttcccttccc agcacagagg    2590
aatattggct ggcatgcaac ctgcaaaaga aaaatgcgaa gcggccgggc acggtggctc    2650
atgcctgtaa tcccagcact ttgggggggct gaggtgggcg aatcatgaga tcaggagttc    2710
gagaccagcc tggccagcat ggtgaaaccc catctctact aaaaatacaa aaaattagct    2770
gggcgtggtg acgggcgcct gtaatcccag atactcagga ggctgaggta ggagaatcac    2830
ttgaacctgg gaggtggaag ttgcagtgaa ccaagatcac gccactgcac tccagcctgg    2890
gcgatggagc gagactccaa ctcaaaaaaa aaaaaaaaa                          2930

<210> SEQ ID NO 2
<211> LENGTH: 536
<212> TYPE: PRT
<213> ORGANISM: Homo sapiens

<400> SEQUENCE: 2

Met Ala Ala Gly Ala Met Thr Pro Pro Arg Pro Val Gln Pro Ala Arg
1               5                   10                  15

Pro Gly Gly Phe Gly Leu Ser Gly Arg Arg Ser Leu Leu Cys Gln Val
            20                  25                  30

Ala Ser Thr Pro Ala His Val Gly Val Met Arg Ser Pro Val Arg Asp
        35                  40                  45

Leu Ala Arg Asn Asp Gly Glu Glu Ser Thr Asp Arg Thr Pro Leu Leu
    50                  55                  60

Pro Gly Ala Pro Arg Ala Glu Ala Ala Pro Val Cys Cys Ser Ala Arg
65                  70                  75                  80

Tyr Asn Leu Ala Ile Leu Ala Phe Phe Gly Phe Phe Ile Val Tyr Ala
                85                  90                  95

Leu Arg Val Asn Leu Ser Val Ala Leu Val Asp Met Val Asp Ser Asn
            100                 105                 110

Thr Thr Leu Glu Asp Asn Arg Thr Ser Lys Ala Cys Pro Glu His Ser
        115                 120                 125

Ala Pro Ile Lys Val His His Asn Gln Thr Gly Lys Lys Tyr Gln Trp
    130                 135                 140

Asp Ala Glu Thr Gln Gly Trp Ile Leu Gly Ser Phe Phe Tyr Gly Tyr
145                 150                 155                 160

Ile Ile Thr Gln Ile Pro Gly Gly Tyr Val Ala Ser Lys Ile Gly Gly
                165                 170                 175

Lys Met Leu Leu Gly Phe Gly Ile Leu Gly Thr Ala Val Leu Thr Leu
            180                 185                 190

Phe Thr Pro Ile Ala Ala Asp Leu Gly Val Gly Pro Leu Ile Val Leu
```

```
            195                 200                 205
Arg Ala Leu Glu Gly Leu Gly Glu Gly Val Thr Phe Pro Ala Met His
210                 215                 220

Ala Met Trp Ser Ser Trp Ala Pro Pro Leu Glu Arg Ser Lys Leu Leu
225                 230                 235                 240

Ser Ile Ser Tyr Ala Gly Ala Gln Leu Gly Thr Val Ile Ser Leu Pro
                245                 250                 255

Leu Ser Gly Ile Ile Cys Tyr Tyr Met Asn Trp Thr Tyr Val Phe Tyr
                260                 265                 270

Phe Phe Gly Thr Ile Gly Ile Phe Trp Phe Leu Leu Trp Ile Trp Leu
            275                 280                 285

Val Ser Asp Thr Pro Gln Lys His Lys Arg Ile Ser His Tyr Glu Lys
290                 295                 300

Glu Tyr Ile Leu Ser Ser Leu Arg Asn Gln Leu Ser Ser Gln Lys Ser
305                 310                 315                 320

Val Pro Trp Val Pro Ile Leu Lys Ser Leu Pro Leu Trp Ala Ile Val
                325                 330                 335

Val Ala His Phe Ser Tyr Asn Trp Thr Phe Tyr Thr Leu Leu Thr Leu
                340                 345                 350

Leu Pro Thr Tyr Met Lys Glu Ile Leu Arg Phe Asn Val Gln Glu Asn
            355                 360                 365

Gly Phe Leu Ser Ser Leu Pro Tyr Leu Gly Ser Trp Leu Cys Met Ile
370                 375                 380

Leu Ser Gly Gln Ala Ala Asp Asn Leu Arg Ala Lys Trp Asn Phe Ser
385                 390                 395                 400

Thr Leu Cys Val Arg Arg Ile Phe Ser Leu Ile Gly Met Ile Gly Pro
                405                 410                 415

Ala Val Phe Leu Val Ala Ala Gly Phe Ile Gly Cys Asp Tyr Ser Leu
                420                 425                 430

Ala Val Ala Phe Leu Thr Ile Ser Thr Thr Leu Gly Gly Phe Cys Ser
            435                 440                 445

Ser Gly Phe Ser Ile Asn His Leu Asp Ile Ala Pro Ser Tyr Ala Gly
450                 455                 460

Ile Leu Leu Gly Ile Thr Asn Thr Phe Ala Thr Ile Pro Gly Met Val
465                 470                 475                 480

Gly Pro Val Ile Ala Lys Ser Leu Thr Pro Asp Asn Thr Val Gly Glu
                485                 490                 495

Trp Gln Thr Val Phe Tyr Ile Ala Ala Ala Ile Asn Val Phe Gly Ala
                500                 505                 510

Ile Phe Phe Thr Leu Phe Ala Lys Gly Glu Val Gln Asn Trp Ala Leu
            515                 520                 525

Asn Asp His His Gly His Arg His
530                 535

<210> SEQ ID NO 3
<211> LENGTH: 2844
<212> TYPE: DNA
<213> ORGANISM: Ovis sp.
<220> FEATURE:
<221> NAME/KEY: CDS
<222> LOCATION: (84)..(1568)

<400> SEQUENCE: 3
cccgggggcg gggggcttcg gcggtcccgc tggagctctc ttttccgcgg agcaggtttg        60
cgccgtagct ccctgaaggc atc atg aag tcc ccg gtt tcg gac tta gcc ccg       113
               Met Lys Ser Pro Val Ser Asp Leu Ala Pro
```

```
                  1                   5                         10
agc gac ggc gag gag ggc tcg gac cgc aca ccg ctc ctg cag cgc gcc    161
Ser Asp Gly Glu Glu Gly Ser Asp Arg Thr Pro Leu Leu Gln Arg Ala
                15                  20                      25 ccg cgg gcg gaa ccc gct cca gta tgc tgc tct gct cgt tac aac cta    209
Pro Arg Ala Glu Pro Ala Pro Val Cys Cys Ser Ala Arg Tyr Asn Leu
            30                  35                      40 gca ttt ttg tcc ttt ttt ggt ttc ttc gtt ctc tat tca tta cgg gtg    257
Ala Phe Leu Ser Phe Phe Gly Phe Phe Val Leu Tyr Ser Leu Arg Val
        45                  50                  55 aat ctg agc gtt gca cta gtg gac atg gtg gat tca aac aca act gcc    305
Asn Leu Ser Val Ala Leu Val Asp Met Val Asp Ser Asn Thr Thr Ala
    60                  65                  70 aaa gat aat aga acg tcc tac gag tgt gca gag cat tct gct ccc ata    353
Lys Asp Asn Arg Thr Ser Tyr Glu Cys Ala Glu His Ser Ala Pro Ile
75                  80                  85                  90 aaa gtt ctt cac aac caa acg ggt aaa aag tac cgg tgg gat gca gaa    401
Lys Val Leu His Asn Gln Thr Gly Lys Lys Tyr Arg Trp Asp Ala Glu
                95                  100                 105 act caa gga tgg att ctc gga tct ttt ttc tat ggc tac atc atc aca    449
Thr Gln Gly Trp Ile Leu Gly Ser Phe Phe Tyr Gly Tyr Ile Ile Thr
            110                 115                 120 caa att cct gga gga tat gtt gcc agc aga agt ggg ggg aag ctg ttg    497
Gln Ile Pro Gly Gly Tyr Val Ala Ser Arg Ser Gly Gly Lys Leu Leu
        125                 130                 135 cta gga ttc ggg atc ttt gct aca gct atc ttc acc ctg ttc act ccc    545
Leu Gly Phe Gly Ile Phe Ala Thr Ala Ile Phe Thr Leu Phe Thr Pro
    140                 145                 150 ctc gct gca gat ttc gga gtc gga gcc ctt gtt gca ctc agg gca cta    593
Leu Ala Ala Asp Phe Gly Val Gly Ala Leu Val Ala Leu Arg Ala Leu
155                 160                 165                 170 gaa ggg cta gga gag ggt gtc aca tat cca gcc atg cat gcc atg tgg    641
Glu Gly Leu Gly Glu Gly Val Thr Tyr Pro Ala Met His Ala Met Trp
                175                 180                 185 tct tca tgg gct ccc cct ctt gaa aga agc aag ctt ctg agt att tca    689
Ser Ser Trp Ala Pro Pro Leu Glu Arg Ser Lys Leu Leu Ser Ile Ser
            190                 195                 200 tat gca gga gca caa ctt ggg aca gta gtt tct ctt cct ctt tct gga    737
Tyr Ala Gly Ala Gln Leu Gly Thr Val Val Ser Leu Pro Leu Ser Gly
        205                 210                 215 gta att tgc tac tat atg aat tgg act tat gtc ttc tat ttc ttt ggc    785
Val Ile Cys Tyr Tyr Met Asn Trp Thr Tyr Val Phe Tyr Phe Phe Gly
    220                 225                 230 att gtt gga atc atc tgg ttt att tta tgg atc tgc tta gtt agt gat    833
Ile Val Gly Ile Ile Trp Phe Ile Leu Trp Ile Cys Leu Val Ser Asp
235                 240                 245                 250 aca cca gaa act cac aag aca atc act ccc tat gaa aag gag tat att    881
Thr Pro Glu Thr His Lys Thr Ile Thr Pro Tyr Glu Lys Glu Tyr Ile
                255                 260                 265 ctt tca tca tta aaa aat cag ctc tct tca cag aag tca gtg ccg tgg    929
Leu Ser Ser Leu Lys Asn Gln Leu Ser Ser Gln Lys Ser Val Pro Trp
            270                 275                 280 ata cct atg ctg aaa tca ctg cca ctt tgg gct att gtc gtt gca cat    977
Ile Pro Met Leu Lys Ser Leu Pro Leu Trp Ala Ile Val Val Ala His
        285                 290                 295 ttt tct tac aac tgg act ttt tat act ttg ttg acc tta ttg cct act   1025
Phe Ser Tyr Asn Trp Thr Phe Tyr Thr Leu Leu Thr Leu Leu Pro Thr
    300                 305                 310 tac atg aag gaa gtc cta agg ttc aat att caa gag aat ggg ttt tta   1073
Tyr Met Lys Glu Val Leu Arg Phe Asn Ile Gln Glu Asn Gly Phe Leu
```

```
                315                 320                 325                 330
tct gca gtc cct tat tta ggt tgt tgg tta tgt atg atc ctg tcg ggt          1121
Ser Ala Val Pro Tyr Leu Gly Cys Trp Leu Cys Met Ile Leu Ser Gly
                    335                 340                 345 caa gct gct gac aat tta agg gca aga tgg aat ttt tca act ctg tgg          1169
Gln Ala Ala Asp Asn Leu Arg Ala Arg Trp Asn Phe Ser Thr Leu Trp
                350                 355                 360 gtt cga aga gtt ttt agc ctt ata ggg atg att gga cct gcg ata ttc          1217
Val Arg Arg Val Phe Ser Leu Ile Gly Met Ile Gly Pro Ala Ile Phe
                    365                 370                 375 ctg gtt gcc gca gga ttt ata ggc tgt gat tat tcc ttg gct gtt gca          1265
Leu Val Ala Ala Gly Phe Ile Gly Cys Asp Tyr Ser Leu Ala Val Ala
                380                 385                 390 ttc cta acc ata tca aca acc ctg gga ggc ttt tgc tct tct gga ttt          1313
Phe Leu Thr Ile Ser Thr Thr Leu Gly Gly Phe Cys Ser Ser Gly Phe
395                 400                 405                 410 agc atc aac cat ctg gac att gct cct tcg tat gct ggt att ctc ctg          1361
Ser Ile Asn His Leu Asp Ile Ala Pro Ser Tyr Ala Gly Ile Leu Leu
                    415                 420                 425 ggc atc aca aat acc ttt gcc act att cct gga atg att ggg ccc atc          1409
Gly Ile Thr Asn Thr Phe Ala Thr Ile Pro Gly Met Ile Gly Pro Ile
                430                 435                 440 att gcc aga agt ctt acc cct gag aac act att gga gaa tgg caa act          1457
Ile Ala Arg Ser Leu Thr Pro Glu Asn Thr Ile Gly Glu Trp Gln Thr
                    445                 450                 455 gtt ttc tgc atc gct gct gct atc aat gta ttt ggt gcc att ttc ttc          1505
Val Phe Cys Ile Ala Ala Ala Ile Asn Val Phe Gly Ala Ile Phe Phe
                460                 465                 470 aca cta ttc gcc aaa ggt gaa gtg caa aac tgg gcc atc agt gat cac          1553
Thr Leu Phe Ala Lys Gly Glu Val Gln Asn Trp Ala Ile Ser Asp His
475                 480                 485                 490 caa gga cac aga aac tgaaggaacc aataaataat cctgtctcta ttaatgtatc         1608
Gln Gly His Arg Asn
                    495 tttgtttatc atgtaaccta aaagtgcctt tgatatttta atgtgtaagc aatctatata       1668 caagataaaa ttgtactaga aaaattgtgt tagatttgta aggcttgtaa tcatgaaatg       1728 tcactagttg ccatataagc aaaattagct attttttaatt attattaacc cgtttgctgg     1788 aacttacaat tcagggtcac atatctggct gcaagtcagg caacccacaa tagggggagtt     1848 ctatttattt ataagaccat acctaaagag atgagctgaa atagacccctt ctataccttt    1908 gcttaattaa ggtggataat aattctcagg tcttgttaaa catctgtttt tgtacaccct     1968 cctcaaaaaa ttatttgtca tcagcaatcc ctgacatgta ggtctcaaac tttagcctct     2028 ccacggagct ggcagccact gtatcattca gcctggcaac ttcactgagg gaagcatgcc     2088 caggcagctg ccacatgtcc cctctctggc ttcagggaca gtgcccagca cttaggcagc     2148 atccaagacc agggtcagcg ccaaggcttt ggacggtatt cttcccctgg ggctgttaat     2208 gtgtggatga agccctgagc caacagggac agcgcgatcc acagtcatgg tttccatgca     2268 ccctctccct tccctcccca gcacactgga gtattgcctg gcatgtaacc tgcaaaagaa     2328 agtgtgatgc ctaattagcc acatataaca tcatccttga tgatcctacc ttcacatgga     2388 tcagagtata aatcttcaag tcctgtgttc taggagctac accagaataa ttaaaatata    2448 aaaagaaaca aaacattttt tctgtctgac acctaagtgt ctggttgcag ttcaaggtta    2508 aagtgacttc tacttcacat aacctgcaac cggtggtgta atcatcttta gtgttggttt    2568 cttaaatctt attttttccag ttttttcctgg accatcttcc agtggtttg agcatgcttt    2628
```

```
gagggcattt atgtgattta gaacttgatt aatgtttcac tgtgtatgtt caacactacc    2688
tgtaatattt taactaaagc tatttaatgt aatatgatgt gtatacattc tgtaaattaa    2748
tttttaaatc tgtaaatagc tttaagttgc tatggtgata tttcttttac aaatcaaaat    2808 aaatctttt ggaatgataa aaaaaaaaaa aaaaaa                               2844
```

<210> SEQ ID NO 4
<211> LENGTH: 495
<212> TYPE: PRT
<213> ORGANISM: Ovis sp.

<400> SEQUENCE: 4

```
Met Lys Ser Pro Val Ser Asp Leu Ala Pro Ser Asp Gly Glu Glu Gly
1               5                   10                  15

Ser Asp Arg Thr Pro Leu Leu Gln Arg Ala Pro Arg Ala Glu Pro Ala
            20                  25                  30

Pro Val Cys Cys Ser Ala Arg Tyr Asn Leu Ala Phe Leu Ser Phe Phe
        35                  40                  45

Gly Phe Phe Val Leu Tyr Ser Leu Arg Val Asn Leu Ser Val Ala Leu
    50                  55                  60

Val Asp Met Val Asp Ser Asn Thr Thr Ala Lys Asp Asn Arg Thr Ser
65                  70                  75                  80

Tyr Glu Cys Ala Glu His Ser Ala Pro Ile Lys Val Leu His Asn Gln
                85                  90                  95

Thr Gly Lys Lys Tyr Arg Trp Asp Ala Glu Thr Gln Gly Trp Ile Leu
            100                 105                 110

Gly Ser Phe Phe Tyr Gly Tyr Ile Ile Thr Gln Ile Pro Gly Gly Tyr
        115                 120                 125

Val Ala Ser Arg Ser Gly Gly Lys Leu Leu Leu Gly Phe Gly Ile Phe
    130                 135                 140

Ala Thr Ala Ile Phe Thr Leu Phe Thr Pro Leu Ala Ala Asp Phe Gly
145                 150                 155                 160

Val Gly Ala Leu Val Ala Leu Arg Ala Leu Glu Gly Leu Gly Glu Gly
                165                 170                 175

Val Thr Tyr Pro Ala Met His Ala Met Trp Ser Ser Trp Ala Pro Pro
            180                 185                 190

Leu Glu Arg Ser Lys Leu Leu Ser Ile Ser Tyr Ala Gly Ala Gln Leu
        195                 200                 205

Gly Thr Val Val Ser Leu Pro Leu Ser Gly Val Ile Cys Tyr Tyr Met
    210                 215                 220

Asn Trp Thr Tyr Val Phe Tyr Phe Phe Gly Ile Val Gly Ile Ile Trp
225                 230                 235                 240

Phe Ile Leu Trp Ile Cys Leu Val Ser Asp Thr Pro Glu Thr His Lys
                245                 250                 255

Thr Ile Thr Pro Tyr Glu Lys Glu Tyr Ile Leu Ser Ser Leu Lys Asn
            260                 265                 270

Gln Leu Ser Ser Gln Lys Ser Val Pro Trp Ile Pro Met Leu Lys Ser
        275                 280                 285

Leu Pro Leu Trp Ala Ile Val Val Ala His Phe Ser Tyr Asn Trp Thr
    290                 295                 300

Phe Tyr Thr Leu Leu Thr Leu Leu Pro Thr Tyr Met Lys Glu Val Leu
305                 310                 315                 320

Arg Phe Asn Ile Gln Glu Asn Gly Phe Leu Ser Ala Val Pro Tyr Leu
                325                 330                 335

Gly Cys Trp Leu Cys Met Ile Leu Ser Gly Gln Ala Ala Asp Asn Leu
```

-continued

```
                340                 345                 350
Arg Ala Arg Trp Asn Phe Ser Thr Leu Trp Val Arg Arg Val Phe Ser
            355                 360                 365

Leu Ile Gly Met Ile Gly Pro Ala Ile Phe Leu Val Ala Ala Gly Phe
            370                 375                 380

Ile Gly Cys Asp Tyr Ser Leu Ala Val Ala Phe Leu Thr Ile Ser Thr
385                 390                 395                 400

Thr Leu Gly Gly Phe Cys Ser Ser Gly Phe Ser Ile Asn His Leu Asp
                405                 410                 415

Ile Ala Pro Ser Tyr Ala Gly Ile Leu Leu Gly Ile Thr Asn Thr Phe
            420                 425                 430

Ala Thr Ile Pro Gly Met Ile Gly Pro Ile Ile Ala Arg Ser Leu Thr
            435                 440                 445

Pro Glu Asn Thr Ile Gly Glu Trp Gln Thr Val Phe Cys Ile Ala Ala
        450                 455                 460

Ala Ile Asn Val Phe Gly Ala Ile Phe Phe Thr Leu Phe Ala Lys Gly
465                 470                 475                 480

Glu Val Gln Asn Trp Ala Ile Ser Asp His Gln Gly His Arg Asn
                485                 490                 495
```

GBS TOXIN RECEPTOR COMPOSITIONS AND METHODS OF USE

CROSS REFERENCE TO RELATED APPLICATIONS

The present application is a continuation-in-part application of U.S. patent application Ser. No. 12/142,060, filed Jun. 19, 2008, which is a divisional application of U.S. patent application Ser. No. 10/823,506, filed Apr. 12, 2004, issued Aug. 12, 2008, as U.S. Pat. No. 7,410,640, which is a divisional application of U.S. patent application Ser. No. 09/359,167, filed Jul. 21, 1999, issued Oct. 12, 2004, as U.S. Pat. No. 6,803,448, which claims the benefit of U.S. Provisional Patent Application Ser. No. 60/093,843 filed Jul. 22, 1998. The present application is a continuation-in-part application of U.S. patent application Ser. No. 12/331,067, filed Dec. 9, 2008, which is a continuation-in-part application of U.S. patent application Ser. No. 09/776,865, filed Feb. 2, 2001, now abandoned, which claims the benefit of U.S. Provisional Patent Application Ser. No. 60/179,870, filed Feb. 2, 2000. All of the foregoing patents and patent applications are incorporated herein by reference in their entirety.

TECHNICAL FIELD

This invention provides methods and compositions for preventing or ameliorating medical conditions arising from the formation of pathological neovasculature. These conditions include cancer, scarring during wound healing, keloid formation, chronic wounds, gliosis during repair of nerve injury, reperfusion injury, rheumatoid arthritis, psoriasis and atherosclerosis.

BACKGROUND

Cancer is the second leading cause of death in the United States, second only to heart disease (which is frequently due in part to atherosclerosis). Since 1990 approximately 12 million new cases of cancer have been diagnosed and five million persons have died of cancer in the United States.

Neural injury can result in death or profound disability such as loss of movement, impaired sensory perception, loss of cognitive functions, seizures, and emotional and personality disorders.

Rheumatoid arthritis (RA) and psoriasis are prevalent chronic inflammatory diseases propagated by inflammatory angiogenesis. RA affects approximately 1-2% of the world's population. RA sufferers often experience pain and impaired mobility, and as a group they have twice the mortality rate of their unaffected counterparts. Approximately 1-3% of United States residents and an even higher percentage of Northern Europeans suffer from psoriasis, a disease in which the skin develops recurrent erythematous plaques that burn and itch.

Chronic wounds or skin ulcers are major problems in diabetic and geriatric populations. Poor healing of acute wounds inflicted by accidents or surgical incisions and the formation of wound-associated scars seriously impair recovery from such events. Reperfusion injuries cause damage to transplanted organs as well as tissues near the site of surgical intervention, stroke or heart attack.

There is a need for a prophylaxis that would prevent cancer, gliosis during repair of nerve injury, chronic inflammatory diseases such as rheumatoid arthritis and psoriasis, scarring during wound healing, keloid formation, chronic wounds, reperfusion injury and atherosclerosis. There is also a need for an effective and safe therapy for each of these medical conditions.

SUMMARY OF THE INVENTION

The present invention provides a method for preventing or protecting against pathoangiogenic conditions by administering one or more Group B β-hemolytic *Streptococci* (GBS) toxin receptors or immunogenic fragments thereof to a mammal in an amount sufficient to induce or maintain an immune response to at least one of the GBS toxin receptors.

The present invention also provides a method for decreasing the incidence of, ameliorating, lessening the severity of, or attenuating pathoangiogenic conditions by administering one or more GBS toxin receptors or immunogenic fragments thereof to a mammal in an amount sufficient to induce or maintain an immune response to at least one of the GBS toxin receptors.

Another aspect of the present invention is a vaccine comprising one or more GBS toxin receptors or immunogenic fragments thereof in combination with a pharmaceutically acceptable excipient.

The pathoangiogenic conditions that can be prevented or attenuated by the methods and compositions of the present invention include cancer, scarring during wound healing, keloid formation, chronic wounds, gliosis during repair of nerve injury, reperfusion injury, rheumatoid arthritis, psoriasis and atherosclerosis.

Preferred GBS toxin receptors are HP59 and SP55 and substantially identical variants thereof. Mammals treated with the methods or the compositions of the present invention may be additionally treated with GBS toxin, with immunocompatible antibodies directed at the GBS toxin receptor, or with autologous activated GBS toxin receptor-recognizing T cells.

Yet another aspect of the present invention is a method for making a composition for the treatment and/or prevention of pathoangiogenic conditions. This method involves providing one or more GBS toxin receptors or immunogenic fragments thereof, and formulating it in a pharmaceutically acceptable excipient. An adjuvant may optionally be provided.

DESCRIPTION OF SPECIFIC EMBODIMENTS

Introduction

Figure 1:
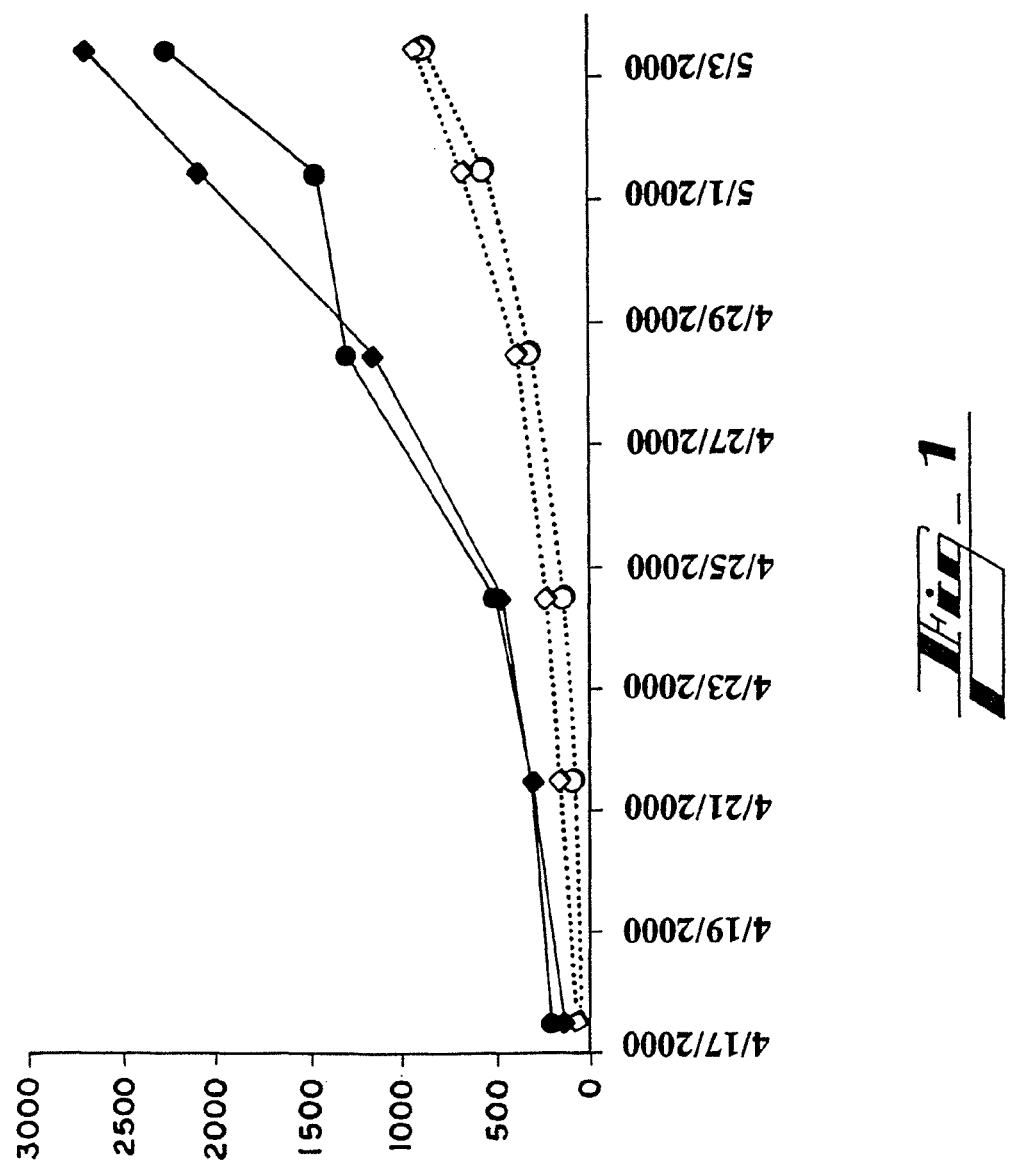
FIG. 1 presents growth curves for Lewis Lung tumors in control mammals and in male and female mammals immunized with a composition of the present invention. The y-axis represents tumor volume and the x-axis represents the day the tumor volume was measured. Male controls are denoted by blackened diamonds, female controls are denoted by blackened circles; male immunized are denoted by clear circles and female immunized are denoted by clear diamonds.

Group B β-hemolytic *Streptococci* (GBS) are ubiquitous microorganisms that are generally harmless to humans with one exception—newborn infants infected with GBS frequently develop GBS pneumonia (also called "early onset disease" or "early onset septicemia"), a disease that is associated with high morbidity and mortality. Hellerqvist and colleagues identified a polysaccharide GBS toxin that is a major factor in the complications of GBS pneumonia (Hellerqvist, C. G. et al., *Pediatr. Res.*, 12:892-898 (1981); Sundell, H. et al., *J. Pediatr.* 137: 338-344 (2000)).

GBS toxin was subsequently found to have many therapeutic properties. It is an anticancer agent that inhibits vascularization of solid tumors (U.S. Pat. No. 5,010,062 and corresponding European Patent No. EP 0 445 280 B1; DeVore et al. (1997) *Clinical Cancer Res.* 3, 365-372)). In addition, as described in U.S. Pat. No. 5,858,991 and WO98/32453, GBS toxin facilitates wound healing in mammals by minimizing scarring and accelerating healing, and reduces wound-related tumor progression. GBS toxin also enhances repair of neural injuries by minimizing the formation of glial scars (U.S. Pat. No. 5,981,508 and WO98/32448) and ameliorates the symptoms of certain chronic inflammatory diseases such as rheumatoid arthritis and psoriasis (WO98/32452).

GBS toxin's anticancer effect has been traced to its ability to rapidly bind tumor-associated endothelial cells and to subsequently activate complement by the alternate (C3) pathway. Activated leukocytes soon infiltrate the endothelial cells, which are subsequently destroyed, and the tumors shrink as a result of the inflammatory response and insufficient blood supply (Yan et al., *Angiogenesis* 2:219-233 (1998); Wamil, B. D. et al., *AACR Proceedings*, 38:237 (1997)).

Without limitation to a particular theory, it is believed that GBS toxin's other therapeutic effects are due to a similar mechanism. Nerve trauma, wounds, disruption of blood flow, reperfusion, atherosclerotic plaques, rheumatoid arthritis and psoriasis all induce hypoxia which in turn causes the release of vascular endothelial growth factor (VEGF) (Liu et al., *J. Neuroscience* 17:5395-5406 (1997)). VEGF stimulates endothelial cells to dedifferentiate and begin forming new vasculature by a process known as pathological angiogenesis and also known as pathoangiogenesis. In patients with neural injuries, the newly formed vasculature facilitates gliosis, a proliferation of glial cells which gives rise to glial scars that sterically interfere with re-establishment of neuronal connectivity. Neovasculature in the joints of rheumatoid arthritis sufferers facilitates synovial tissue hyperplasia, pannus formation, and cartilage destruction. Similarly, pathological angiogenesis facilitates the establishment, maintenance and enlargement of psoriatic lesions and is a driving force in the formation of granulation tissue, which leads to chronic wounds or scar formation (including keloids) in the vicinity of wounds. In atherosclerosis, the pathological neovasculature provides oxygen and nutrients to smooth muscle and endothelial cells located below plaques and results in further narrowing of affected blood vessels. Other conditions caused by pathological angiogenesis include diabetic retinopathy, retrolental fibroplasia, neovascular glaucoma, angiofibromas, immune and non-immune inflammation, hemangiomas, Kaposis' sarcoma, and endometriosis (see PCT Publication Number WO 91/10424, page 13, lines 14-21). Additional conditions caused by pathological angiogenesis include corneal graft neovascularization, ocular tumors, trachoma, and hemophiliac joints (see European Patent Application Publication Number EP 0 325 199 A2, page 2, lines 12-19). Additional conditions caused by pathological angiogenesis include retinopathy of prematurity, macular degeneration, Behcet's syndrome, Osler-Weber-Rendu disease, osteoarthritis, corneal graft rejection and ocular neovascular diseases (see PCT Publication Number WO 94/20085, page 2, line 27 to page 6, line 14). GBS toxin interferes with these harmful processes by binding to the budding pathological neovasculature and targeting it for destruction by the immune system.

It was believed that GBS toxin attacks the lungs of human neonates and binds embryonic neovasculature via receptors present on these tissues at birth and for a short time (about 7 days in term babies and longer in premature infants) thereafter. It was further hypothesized that the same receptors are present later in life only upon pathological neovasculature (i.e. new capillaries formed by pathological angiogenesis). This belief has been confirmed by the recent identification of novel proteins found on such cells that specifically bind GBS toxin. The nucleic acid and amino acid sequences of the human GBS toxin receptor known as HP59 are shown in SEQ ID NO:1 and SEQ ID NO:2, respectively (GenBank Accession Number AF244578). The nucleic acid and amino acid sequences of the sheep GBS toxin receptor known as SP55 (cloned from a sheep lung library, GenBank Accession Number AF244578) are shown in SEQ ID NO:3 and SEQ ID NO:4, respectively. Both HP59 and SP55 are integral proteins with multiple transmembrane domains. Each has several putative sites for phosphorylation by cAMP-dependent kinase, protein kinase C (PKC) and casein kinase II (CK2) as well as putative sites for glycosylation and myristylation. Although HP59 has 41 amino acids at its amino terminus that SP55 lacks, the two proteins are otherwise 87% identical.

As expected, GBS toxin receptor is expressed on the lungs of human neonates and sheep (which are susceptible to infection by GBS). It is not expressed in the vasculature associated with normal (healthy, non-neonate) human ovary, colon, breast or lung tissue, but it is present in the vasculature of tumors in these tissues. Thus, GBS toxin receptor expression is correlated with medical conditions involving pathologic angiogenesis and the receptor is not seen in healthy tissue from humans who are more than one month old (except for premature babies, in which expression is correlated with their due dates).

Although not wishing to be bound by theory, it is believed that since the GBS toxin receptor is present on the pathological neovasculature associated with pathoangiogenic conditions, the immune system, if primed to recognize the GBS toxin receptor, will attack such forming vasculature and the pathoangiogenic condition will be prevented or attenuated. Therefore, the present invention involves methods and compositions for invoking an immune response to the GBS toxin receptor.

Definitions

Generally, all technical and scientific terms used herein have the same meaning as commonly understood by one of ordinary skill in the art to which this invention belongs. The nomenclature used herein and the laboratory procedures in immunology, cell culture, biochemistry and molecular biology described below are those well known and commonly employed in the art. Standard techniques are used for recombinant nucleic acid methods, polypeptide synthesis, and production of monoclonal and polyclonal antibodies. Enzymatic reactions and purification steps supplied by manufacturers are typically performed according to the manufacturer's specifications. The techniques and procedures are generally performed according to conventional methods in the art and various general references (See generally, Sambrook et al., *Molecular Cloning: A Laboratory Manual*, 2d ed. (1989) Cold Spring Harbor Laboratory Press, Cold Spring Harbor, N.Y.) which are provided throughout this document. The nomenclature used herein and the laboratory procedures in analytical chemistry, organic synthetic chemistry, immunology and, pharmaceutical formulation described below are those well known and commonly employed in the art. Standard techniques can be used for chemical syntheses, chemical analyses, pharmaceutical formulation and delivery, and treatment of mammals. As employed throughout the disclosure, the following terms, unless otherwise indicated, shall be understood to have the following meanings:

For the purposes of this invention, the term "GBS toxin" means any purified fraction or component of the natural GBS toxin, or derived from media or protease digests of lysed GBS bacterial, and whose toxicity can be confirmed by either of the following specified assay procedures. The potency of isolated GBS toxin as a tumor growth inhibitor may be ascertained by peroxidase-antiperoxidase (PAP) assays of tumor tissue specimens using anti-GBS toxin IgG, and by infusion in a sheep model at 2 μgs $10^{-11}$ moles per kg (Hellerqvist, C. G. et al., 1981, cited above; Hellerqvist, C. G. et al. *PNAS* 84:51-56 (1987)).

"GBS toxin receptor" means a proteinaceous molecule capable of binding a toxin from Group B β-hemolytic *Streptococcus* bacteria (GBS toxin). A GBS toxin receptor is usually found in nature on the surface of a cell. Recombinant membrane-bound and soluble GBS toxin receptors can be produced by laboratory techniques known in the art. GBS toxin receptor refers to any receptor that interacts with a GBS toxin as defined herein.

As used herein, a vaccine or method is said to "prevent" or "protect against" a medical condition if its administration to an individual results in the failure of the individual to develop the medical condition.

As used herein, a vaccine or method is said to "ameliorate," "attenuate" or "lessen the severity of" a medical condition if its administration to an individual results either in the suppression or partial suppression of at least one symptom or other manifestation of the medical condition in the individual.

As used herein, a vaccine or method is said to "decrease the incidence of" a medical condition if its administration to an individual has the effect of decreasing the probability that the individual will develop the medical condition.

A "pathoangiogenic condition" is any medical condition associated with pathological angiogenesis such as that caused by for instance the hypoxia-induced, VEGF-mediated formation of new vasculature from dedifferentiated endothelial cells. Pathological angiogenesis occurs in such diseases as diabetic retinopathy, hemangioma, cancer, psoriasis, RA, osteoarthritis and atherosclerosis. (Folkman et al., *Science,* 235:442 (1987); Kimball et al., *Agents & Actions,* 34:329 (1991)). It is also is associated with the formation of glial scars in the vicinity of injured nerves and in the formation of keloids, reperfusion injuries and scars during wound healing. Pathological angiogenesis is distinct from physiological neovascularization, a basic repair mechanism that occurs under normal, healthy circumstances (such as wound healing, the female menstrual cycle, and pregnancy) and is believed to result from the proliferation of existing endothelial cells after the disruption of contact inhibition (Brem & Folkman, *J. Ped. Surg.,* 28:445 (1993)).

An "immune response" may be humoral or cell-mediated or both. In a humoral response, the immunized animal produces antibodies that recognize and specifically bind a particular antigen. Preferably, the titer for such antibodies would be at least about 1:200 as measured by ELISA. A cell-mediated immune response is characterized by the presence of helper T cells, suppressor T cells, and/or cytotoxic T cells that recognize the antigen. The presence of such cells can be confirmed by methods known in the art, including the development of a raised area of at least 1 mm within 72 hours after the subcutaneous administration of a sample of the antigen.

As used in the context of an antibody administered to a mammal, such an antibody is "immunocompatible" with such mammal if the mammal's immune system does not treat it as a foreign protein and mount an immune response against it. The antibody to be administered may be obtained from a mammal of the same species as the recipient mammal. Alternatively, such antibody can be engineered to contain constant regions that resemble those of antibodies naturally produced by the recipient mammal. Where the recipient mammal is a human, such antibodies are frequently referred to as "humanized" antibodies.

The term "immunogenic" means having antigenic properties or being capable of being specifically bound by an antibody that can specifically bind the antigen. A substance has antigenic properties if it can generate or is capable of eliciting an immune response when administered to an animal under conditions known in the art to facilitate the production of antibodies and/or T cells that will recognize and elicit a cytotoxic response toward cells expressing the particular antigen.

The term "adjuvant" refers to an agent used to enhance the immune response of an immunized mammal to an antigen.

The term "parenteral" as used herein includes subcutaneous injections, intraperitoneal or intramuscular injection, or infusion techniques.

The term "polypeptide" is used herein as a generic term to refer to native protein, fragments, analogs, or glycosylated, phosphorylated or myristylated isoforms of a polypeptide sequence. Hence, native protein, fragments, analogs and glycosylated, phosphorylated and myristylated isoforms are species of the polypeptide genus.

The term "isolated" as used herein in the context of a polypeptide means a polypeptide that is no longer associated with the cell that the polypeptide is normally associated with in nature in the same manner as it is normally associated in nature, such as (1) a polypeptide free of at least some other polypeptides from the same source, (2) a polypeptide expressed by a cell from a different species, (3) a polypeptide that does not occur in nature, and (4) a polypeptide produced from cDNA, recombinant RNA, or synthetic origin or some combination thereof.

The term "naturally occurring" means found in nature. For example, a polypeptide or polynucleotide sequence that is present in an organism (including viruses) found in nature and which has not been intentionally modified in the laboratory is naturally occurring.

As applied to polypeptides, the term "substantial identity" means that two peptide sequences, when optimally aligned by the BLAST computer program, share at least about 80 percent sequence identity, at least about 86 percent sequence identity, and preferably at least about 90 percent sequence identity. Gaps (in either of the two sequences being matched) are allowed in maximizing matching; gap lengths of about 10 or less are preferred, with about 5 or less being more preferred. Residue positions which are not identical may differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine.

In one example, an amino acid sequence of a polypeptide may differ from SEQ ID NO:2 at no more than about 20% of the amino acid residues. In another example, an amino acid sequence of the polypeptide may differ from SEQ ID NO:2 at no more than about 1% of the amino acid residues. In one more example, an amino acid sequence of a polypeptide may differ from SEQ ID NO:2 by one amino acid. In another example, GBS toxin receptor polypeptide can be encoded by a nucleic acid sequence greater than 95% sequence identity to SEQ ID NO:1.

The term "fragment" as used herein refers to a peptide that has an amino-terminal, internal and/or carboxy-terminal deletion, but where the remaining amino acid sequence is identical to the corresponding positions in the naturally occurring sequence deduced, for example, from a full-length DNA sequence. Fragments typically are at least about 3 amino acids long, preferably are about 5-10 amino acids long, more preferably are about 10-50 amino acids long, and even more preferably are more than about 50 amino acids long. Also preferred are fragments that comprise one or more extracellular domains of a GBS toxin receptor. Such fragments may also comprise portions of transmembrane and intracellular domains sufficient to maintain the polypeptide fragment in a stereochemical conformation on the surface of a cell, lipid membrane, liposome, micelle, or other lipophilic structure.

The singular forms "a," "an" and "the" include plural referents unless the context clearly dictates otherwise.

The SEQ ID NOs of the nucleic acid and amino acid sequences described herein are summarized below in Table 1.

TABLE 1

Nucleic Acid and Amino Acid Sequences

| SEQ ID NO: | Type of Sequence | Description |
|---|---|---|
| SEQ ID NO: 1 | Nucleic acid | Full-length human GBS toxin receptor (HP59) |
| SEQ ID NO: 2 | Amino acid | Full-length human GBS toxin receptor (HP59) |
| SEQ ID NO: 3 | Nucleic acid | Sheep GBS toxin receptor (SP55) |
| SEQ ID NO: 4 | Amino acid | Sheep GBS toxin receptor (SP55) |

The headings provided herein describe the general topic discussed and are not intended to be exclusive of information discussed in other sections. Frequently, information, methods, compositions, and other aspects may be applicable to more than one embodiment of the invention and can be so combined.

One aspect of the present invention is a method for preventing a pathoangiogenic condition in a mammal by administering to the mammal an amount of one or more GBS toxin receptors or immunogenic fragments thereof effective to induce or maintain in the mammal an immune response to at least one of the GBS toxin receptors.

Another aspect of the present invention is a method for attenuating a pathoangiogenic condition in a mammal by administering to the mammal an amount of one or more GBS toxin receptors or immunogenic fragments thereof effective to induce or maintain in the mammal an immune response to at least one of the GBS toxin receptors. This method may be performed at a time when the mammal does not have any symptoms of the pathoangiogenic condition. Such administration serves to lessen the severity or progression of the subsequently developed pathoangiogenic condition. When the method is performed on a mammal suffering from the pathoangiogenic condition, it will ameliorate one or more symptoms of the pathoangiogenic condition.

The aforementioned methods may be performed on any animal that expresses a GBS toxin receptor on pathological neovasculature. Preferably, such animal is a mammal that does not express the receptor on healthy tissues. It is known that human embryos and full-term newborn babies up to about 10 days old have GBS toxin receptors on their lung vasculature. Sheep, cows and cats express GBS toxin receptors on their lung vasculature shortly after birth and thereafter. Preferred recipients of this method are full-term humans older than ten days, dogs, mice, pigs, goats and horses.

In other embodiments of the invention, immunized animals receive antibodies to GBS toxin receptor or immunogenic fragments thereof, or expanded autologous T cells to GBS toxin receptor, or combinations thereof. These methods may be used to attack the vasculature in pathoangiogenic conditions. These embodiments may be used independently of each other, or in combination with the treatments disclosed herein for pathoangiogenic diseases, or in combination with other treatments for pathoangiogenic diseases used in the art.

For example, as stated earlier, it was believed that GBS toxin attacks the lungs of human neonates and binds embryonic neovasculature via receptors present on these tissues at birth. GBS toxin was subsequently found to inhibit vascularization of solid tumors and ameliorate the symptoms of other diseases. Therefore, in another embodiment of the invention, in addition to receiving at least one GBS toxin receptor or at least one immunogenic fragment thereof, immunized animals also receive GBS toxin or fragments thereof, antibodies to at least one GBS toxin receptor or immunogenic fragments thereof, or expanded autologous T cells or combinations thereof. The supplemental treatments are preferred when the animal is at high risk for or is currently suffering from a pathoangiogenic condition. GBS toxin may be obtained from CarboMed, Inc. (Brentwood, Tenn.) or may be purified as taught in U.S. Pat. Nos. 5,010,062 and 5,811,403 and WO98/14603, which are hereby incorporated by reference. For human recipients, GBS toxin is preferably administered in amounts in the range of about 5 µg/kg to about 25 µg/kg. Methods for administering GBS toxin for the treatment of the following pathoangiogenic conditions are taught in the following patents which are herein incorporated by reference:

| Condition(s) | Patent |
|---|---|
| Cancer | U.S. Pat. No. 5,010,062 |
| Scarring | U.S. Pat. No. 5,858,991 |
| Keloids | U.S. Pat. No. 5,858,991 |
| Reperfusion injury | U.S. Pat. No. 5,858,991 |
| Atherosclerosis | U.S. Pat. No. 5,858,991 |
| Burns | U.S. Pat. No. 5,858,991 |
| Chronic wounds | U.S. Pat. No. 5,858,991 |
| Gliosis | U.S. Pat. No. 5,981,508 |
| Rheumatoid arthritis | WO98/32452 |
| Psoriasis | WO98/32452 |

Antibodies to the GBS toxin receptor can be obtained by immunizing animals including rabbits, mice, goats and chickens with the GBS toxin receptor or an immunogenic fragment thereof. Monoclonal antibodies, polyclonal antibodies and variants thereof can be used. Examples of variants include, but are not limited to, single-chain (recombinant) antibodies, "humanized" chimeric antibodies, and immunologically active fragments of antibodies (e.g., Fab and Fab' fragments). The production of non-human monoclonal antibodies, e.g., murine, is well known (see, e.g., Harlow et al., *Antibodies A*

Laboratory Manual, Cold Spring Harbor Press, pp. 139-240, 1989). Immunocompatible antibodies are preferred to prevent the immunized animal from mounting an immune response to the GBS toxin receptor antibodies. To prepare antibodies that are immunocompatible to a human, it is desirable to transfer antigen binding regions of non-human monoclonal antibodies, e.g. the F(ab')$_2$ or hypervariable regions of murine monoclonal antibodies, to human constant regions (Fc) or framework regions by recombinant DNA techniques to produce substantially human molecules. Such methods are generally known and are described in, e.g., U.S. Pat. Nos. 4,816,397 and 4,946,778, and EP publications 173,494 and 239,400. Alternatively, one may isolate DNA sequences which code for a human monoclonal antibody or portions thereof that specifically bind to the receptor protein by screening a DNA library from human B cells according to the general protocol outlined in WO 90/14430, and then cloning and amplifying the sequences which encode the antibody (or binding fragment) of the desired specificity. These sequences may be inserted into the DNA of a mammal in such a manner that the mammal will secrete the antibodies into its milk (Genzyme Transgenics, Framingham, Mass.). Such antibodies may be administered intraperitoneally or intravenously. Alternate regimens can be determined by one of skill in the art using the basic principles discussed under "Administration" below.

The antibodies can also be used to develop a method of targeting a cytotoxic agent for delivery to a cell that expresses a GBS toxin receptor. For example, a cytotoxic agent can be coupled to an antibody that binds a GBS toxin receptor for selective delivery to the neovasculature of a growing tumor. Such a delivery system would permit a highly concentrated, localized attack on a growing tumor, while minimizing the adverse systemic side effects encountered with most chemotherapeutics.

The sections that follow address in greater detail the selection of immunogenic fragments of the GBS toxin receptor, the production of the receptor polypeptide, identification of other GBS toxin receptors, composition preparations, vaccine preparations, pharmaceutical compositions, administration of the compositions or vaccines, and monitoring of immune response.

Immunogenic Peptides of the GBS Toxin Receptor

One embodiment of the'present invention involves the administration of one or more immunogenic fragments of a GBS toxin receptor. Preferred receptors are HP59 and SP55 and preferred fragments include the Hab1, Hab2 and Hab3 peptides shown in Table 3 and used in Example 1. Preferably the mammal receives a combination of at least two immunogenic fragments and more preferably all three such fragments. Co-administration of fragments from HP59 and SP55 may be desirable to elicit a robust immune response. The immunogenic fragments may contain naturally occurring post-translation modifications such as glycosylation, myristylation or phosphorylation. Other immunogenic fragments of a GBS toxin receptor may be administered in the present invention and one of skill in the art can readily identify appropriate fragments using techniques known in the art.

A number of methods has been developed to predict the location of immunogenically important epitopes on proteins. The outcome of the combined predictions gives a good forecast of antigenic sites. Suitable GBS toxin receptor fragments may be selected, for instance, from the most hydrophilic parts of the receptor, e.g. by applying the technique described by Hopp and Woods (T. P. Hopp and K. R. Woods (1981): Proc. Natl. Acad. Sci, U.S.A. 78, 3824-3828). Another suitable method for selecting immunogenic fragments is described by Chou and Fasman (P. Y. Chou and G. D. Fasman (1987) Advances in Enzymology 47, 45-148). Various additional algorithms can be used to predict the antigenically important regions of the GBS toxin receptor, such as a prediction of the flexibility of the polypeptide chain (P. A. Karplus and G. E. Schultz, 1985, Naturwissenschafien 72, 212-213), a beta-turn probability profile (P. Y. Chou and G. D. Fasman, 1979, Biophys. J. 26, 367-385), the probability profiles in the 3 conformations for the sequence (Gascuel, O. and J. L. Golmard, 1988, CABIOS 4, 357-365), a prediction of the secondary structure of the sequence (J. Novotny and C. Auffray, 1984, Nucleic Acids Research 12, 243-255). Additional information on the location of relevant epitopes can be obtained using the PEPSCAN-method, developed by Geysen and Meloen (H. M. Geysen, R. H. Meloen and S. J. Barteling (1984) Proc. Natl. Acad. Sci., U.S.A. 81(13); 3998-4002). All of these techniques can be used to select suitable GBS toxin receptor fragments for use as immunogenic antigens in the present invention.

In addition, immunoreactive epitopes of the GBS toxin receptor can be identified by expressing DNA fragments from the GBS toxin receptor gene in suitable plasmids, such as the pEX plasmids (K. Stanley and J. P. Luzio, 1984. EMBO J. 3, 1429-1434, and J. G. Kusters, E. J. Jager and B. A. M. Van der Zeijst, 1989. Nucl. Acids Res., 17, 8007). In this system, heterologous expression leads to the synthesis of a C-terminal extension of the cro-β-galactosidase hybrid protein. Restriction-endonuclease sites in the GBS toxin receptor DNA sequence can be used to obtain fragments of the GBS toxin receptor gene for insertion into the pEX plasmids. pEX clones synthesizing fusion proteins derived from different overlapping regions of the GBS toxin receptor are then used for further characterization. The GBS toxin receptor fragments are purified, fractionated by polyacrylamide gel electrophoresis, and blotted to nitrocellulose membranes. These membranes are then reacted with polyclonal antibodies directed at the GBS toxin receptor. Only the fragments containing the immuno-reactive epitopes will react with these antibodies. To delineate the minimal length of the epitopes, the DNA inserts of the reactive clones can be progressively shortened by Exonuclease III digestion, or by cloning synthetic oligonucleotides encoding small overlapping parts of the GBS toxin receptor (J. G. Kusters, E. J. Jager, G. Koch, J. A. Lenstra. W. P. A. Posthumus, R. H. Meloen and B. A. M. Van der Zeijst, 1989. J. Immunol., 143, 2692-2698). The epitopes can then be tested for their abilities to generate an immune response in the mammal of choice. Such testing can be performed using methods known in the art as well as methods described in the "Monitoring Immune Response" section of this application.

Using the method of Hopp and Woods via the "Antigen" program in PC/GENE, Hellerqvist and colleagues have identified three regions of SP55, shown below in Table 2, as having high hydrophilicity and as likely to be immunogenic.

TABLE 2

| | High Points of Hydrophilicity in SP55 | |
|---|---|---|
| No. | Average Hydro- philicity | Sequence |
| 1 | 2.05 | Glu-Glu-Gly-Ser-Asp-Arg (residues 14-19 of SEQ ID NO: 4) |
| 2 | 1.52 | Lys-Asp-Asn-Arg-Thr-Ser (residues 75-80 of SEQ ID NO: 4) |

TABLE 2-continued

High Points of Hydrophilicity in SP55

| No. | Average Hydro-philicity | Sequence |
|---|---|---|
| 3 | 1.33 | Arg-Ala-Pro-Arg-Ala-Glu (residues 25-30 of SEQ ID NO: 4) |

Hellerqvist and colleagues have successfully prepared mouse monoclonal antibodies directed to the portions of HP59 shown in Table 3 and rabbit polyclonal antibodies directed at the peptides from SP55 shown in Table 4. The rabbit polyclonal antibodies bind both SP55 and HP59 and several of the hybridomas produce monoclonal antibodies that recognize both SP55 and HP59.

TABLE 3

Immunogenic Peptides from HP59

| Peptide | Amino Acid Sequence | Size | SEQ ID Ref. |
|---|---|---|---|
| Hab1 | LARNDGEESTDRTPL | 15 aa | residues 49-63 of SEQ ID NO: 2 |
| Hab2 | NTTLEDNRTSKACP | 14 aa | residues 112-125 of SEQ ID NO: 2 |
| Hab3 | PPRPVQPARPGGFGLSGRRSL | 21 aa | residues 8-28 of SEQ ID NO: 2 |
| Hab4 | LARNDGEESTDRTPLLPGAPR AEAAPVC | 28 aa | residues 49-76 of SEQ ID NO: 2 |

TABLE 4

Immunogenic Peptides from SP55

| Peptide | Amino Acid Sequence | Size | SEQ ID Ref. |
|---|---|---|---|
| p56a | APSDGEEGSDRTPLL QRAPRAEPAPVC | 27 aa | residues 9-35 of SEQ ID NO: 4 |
| p55a[1] | LAPSDGEEGSDRTPL | 15 aa | residues 8-22 of SEQ ID NO: 4 |
| p57a[2] | NTTAKDNRTSYECA | 14 aa | residues 71-84 of SEQ ID NO: 4 |

[1]Peptide p55a is a fragment of an extracellular domain of GBS toxin receptor.
[2]Peptide p57a is a fragment of an intracellular domain of GBS toxin receptor.

Preparation of GBS Toxin Receptor Polypeptides

The GBS toxin receptor polypeptides of the present invention may be utilized in an unmodified state. Alternatively, the polypeptides may be glycosylated, myristylated, or phosphorylated at one or more of the putative sites for such post-translational modifications. The GBS toxin receptor protein or polypeptides may be prepared as homopolymers (a multitude of identical GBS toxin receptor polypeptides coupled) or heteropolymers (one or more GBS toxin receptor polypeptides coupled to one or more different GBS toxin receptor polypeptides), or may be coupled to one or more other compounds in order to enhance immunogenicity.

In one embodiment of the invention, the GBS toxin receptor protein is naturally occurring and can be isolated from a cell extract by protein purification techniques known in the art, such as, for example, ion exchange column chromatography, high performance liquid chromatography (HPLC), reverse phase HPLC, or affinity chromatography using antibodies that recognize the GBS toxin receptor. The purified protein can be optionally lyophilized and stabilized.

In another embodiment, the GBS toxin receptor or polypeptide fragments from it can be synthesized chemically by techniques well known in the art, such as solid-phase peptide synthesis (Stewart et al., SOLID PHASE PEPTIDE SYNTHESIS, W.H. Freeman Co., San Francisco (1963)); Merrifield, *J. Am. Chem. Soc.* 85:2149-2154 (1963)). These and other methods of peptide synthesis are also exemplified by U.S. Pat. Nos. 3,862,925, 3,842,067, 3,972,859, and 4,105,602. The synthesis can use manual synthesis techniques or automatically employ, for example, an Applied BioSystems 430A or 431A Peptide Synthesizer (Foster City, Calif.) following the instructions provided in the instruction manual supplied by the manufacturer.

Alternatively, the polypeptides can be expressed using polynucleotides encoding the polypeptide(s) in operative association with an appropriate control sequence including a promoter in an expression vector suitable for expression, preferably in a mammalian cell, and also in bacterial, insect, or yeast cells. Preferably, the GBS toxin receptor polynucleotide or a fragment thereof can be expressed in a mammalian system. Such expression will usually depend on a mammalian promoter, which is any DNA sequence capable of binding mammalian RNA polymerase and initiating the downstream (3') transcription of a coding sequence (e.g. structural gene) into mRNA. Usually, a promoter will have a transcription initiation region which is usually placed proximal to the 5' end of the coding sequence. This transcription initiation region typically includes an RNA polymerase binding site and a transcription initiation site.

Vectors suitable for replication in mammalian cells are known in the art, and can include viral replicons, or sequences that ensure integration of the sequence encoding PAK65 into the host genome. Suitable vectors can include, for example, those derived from simian virus SV40, retroviruses, bovine papilloma virus, vaccinia virus, and adenovirus. A suitable vector, for example, is one derived from vaccinia viruses. In this case, the heterologous DNA is inserted into the vaccinia genome. Techniques for the insertion of foreign DNA into the vaccinia virus genome are known in the art, and utilize, for example, homologous recombination. The insertion of the heterologous DNA is generally into a gene that is non-essential in nature, for example, the thymidine kinase gene (tk), which also provides a selectable marker. Plasmid shuttle vectors that greatly facilitate the construction of recombinant viruses have been described (see, for example, Mackett et al. (1984); Chakrabarti et al. (1985); Moss (1987)). Expression of the heterologous polypeptide then occurs in cells or individuals which are immunized with the live recombinant vaccinia virus.

A specific case of the above embodiment is a so-called vector vaccine in which recombinant polynucleotide are produced in the immunized animal via viral vectors. The viruses applicable for this purpose should have the ability to replicate in the animals to be immunized. These viruses, furthermore, should possess a genomic region suitable for insertion of the GBS toxin receptor protein or polypeptide gene. Suitable viruses for this purpose are for example enteral viruses such as certain adeno viruses. A particular application of the present invention is concerned with bacterial vector vaccines in which bacteria capable of colonizing the mammal (e.g. *Salmonella* bacteria) are transformed in order to enable them to express a GBS toxin receptor polypeptide in such a way that it will lead to an immunogenic response against the GBS toxin receptor.

Suitable mammalian expression vectors usually contain one or more eukaryotic transcription units that are capable of facilitating expression in mammalian cells. The transcription unit is comprised of at least a promoter element to mediate transcription of foreign DNA sequences. Suitable promoters for mammalian cells are known in the art and include viral promoters such as those from simian virus 40 (SV40) (Subramani et al., *Mol. Cell. Biol.* 1:854-864, 1981), cytomegalovirus (CMV) (Boshart et al., Cell 41:521-530, 1985), Rous sarcoma virus (RSV), adenovirus (ADV) (Kaufman and Sharp, *Mol. Cell. Biol.* 2:1304-1319, 1982), and bovine papilloma virus (BPV), as well as cellular promoters, such as a mouse metallothionein-1 promoter (U.S. Pat. No. 4,579,821), a mouse VK promoter (Bergman et al., *Proc. Natl. Acad. Sci. USA* 81:7041-7045, 1993; Grant et al., *Nuc. Acids Res.* 15:5496, 1987), and a mouse VH promoter (Loh et al., *Cell* 33:85-93, 1983).

The optional presence of an enhancer element (enhancer), combined with the promoter elements described herein, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when they are placed upstream or downstream from the transcription initiation site, in either normal or flipped orientation, or at a distance of more than 1000 nucleotides from the promoter (Maniatis et al. (1987) *Science* 236:1237; Alberts et al. (1989) MOLECULAR BIOLOGY OF THE CELL, 2nd ed.). Enhancer elements derived from viruses can be particularly useful, because they typically have a broader host range. Examples useful in mammalian cells include the SV40 early gene enhancer (Dijkema et al. (1985) *EMBO J.* 4:761) and the enhancer/promoters derived from the long terminal repeat (LTR) of the Rous Sarcoma Virus (Gorman et al. (1982b) *Proc. Natl. Acad. Sci.* 79:6777), from human cytomegalovirus (Boshart et al. (1985) *Cell* 41:521) as well as the mouse μ enhancer (Gillies, *Cell* 33:717-728, 1983). Additionally, some enhancers are regulatable and become active only in the presence of an inducer, such as a hormone or metal ion (Sassone-Corsi and Borelli (1986) *Trends Genet.* 2:215; Maniatis et al. (1987) *Science* 236: 1237).

In addition, the transcription unit can also be comprised of a termination sequence and a polyadenylation signal which are operably linked to the GBS toxin receptor coding sequence. Polyadenylation signals include, but are not limited to, the early or late polyadenylation signals from SV40 (Kaufman and Sharp), the polyadenylation signal from the Adenovirus 5 E1B region and the human growth hormone gene terminator (DeNoto et al., *Nuc. Acids Res.* 9:3719-3730, 1981).

Sequences that cause amplification of the gene may also be desirable, as are sequences which encode selectable markers. Selectable markers for mammalian cells are known in the art, and include, for example, thymidine kinase, dihydrofolate reductase (together with methotrexate as a DHFR amplifier), aminoglycoside phosphotransferase, hygromycin B phosphotransferase, asparagine synthetase, adenosine deaminase, and antibiotic resistant genes such as neomycin.

A GBS toxin receptor, or fragment thereof, can be expressed on the surface of a cell, or can be expressed in soluble or secreted form. Expression on the surface of the cell can be achieved, for example, by including a secretory leader operably linked to a nucleic acid sequence encoding the desired receptor fragment and at least one transmembrane domain. The secretory leader can be that encoded by the GBS toxin receptor gene, or can be a heterologous leader sequence commonly used in the art, such as, for example, the leader sequence of *Schizosaccharomyces pombe* pho1$^+$ acid phosphatase (Braspenning et al., *Biochem Biophys Res. Commun.* (1998) 245:166-71), the leader sequence of human interleukin-2 (IL-2) gene (Sasada et al., *Cell Struct Funct* (1988) 13:129-141). Expression in soluble or secreted form can be achieved, for example, by excluding from the gene construct nucleic acid sequences encoding a transmembrane domain. In some instances, solubility and/or secretion are achieved by the use of a fusion partner, such as, for example, chloramphenicol acetyltransferase (CAT), β-galactosidase, and other genes readily expressed in the selected host cell.

The vector that encodes GBS toxin receptor can be used for transformation of a suitable mammalian host cell. Transformation can be by any known method for introducing polynucleotides into a host cell, including, for example packaging the polynucleotide in a virus and transducing a host cell with the virus or by transfection procedures known in the art, as exemplified by U.S. Pat. Nos. 4,399,216, 4,912,040, 4,740,461, and 4,959,455. The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including, but not limited to, Chinese hamster ovary (CHO) cells, HeLa cells, baby hamster kidney (BHK) cells, monkey kidney cells (COS), N1E-115 (Liles et al., *J. Biol. Chem.* 261:5307-5313, 1986), PC 12 human hepatocellular carcinoma cells (e.g., Hep G2), and a number of other cell lines, such as insect derived cell lines IF9 and IF21. Cell lines of particular preference are those expressing recombinant GBS toxin receptor constructs constitutively, lines which subsequently develop characteristics of a transformed cell, and lines that more preferably express GBS toxin receptor or fragments on the cell surface. Particularly preferred are ECV cells (a bladder carcinoma cell line originally referred to in the scientific literature as an endothelial cell line), human umbilical vein endothelial cells (HUVEC), bovine, sheep, and human adrenal medulla endothelial cells.

Recombinant GBS toxin receptor or fragments thereof can be produced by culturing host cells expressing the receptor or fragment in a suitable culture medium and under appropriate cell culture conditions. Culture media and conditions are variable depending on the requirements of a particular host cell line and are well known in the art. Typically, cells are cultured at 37° C. in a cell culture incubator with a fixed amount of $CO_2$, usually in the range of 5-10%.

Identification of Other GBS Toxin Receptors

In addition to the preferred GBS toxin receptors HP59 and SP55, other naturally occurring GBS toxin receptors can be used in methods, compositions and vaccines of the present invention. Nucleic acids encoding such receptors can be isolated from various tissue sources and cell cultures from different species that produce such a receptor by the methods described herein, such as, for example, cells from tumor endothelium, synovial tissue in rheumatoid arthritis, or hypoxic tissue deprived of or restricted from blood flow, such as in reperfusion injury or wounded tissue. Such polynucleotides can be isolated by hybridization using probes or by polymerase chain reaction using oligonucleotides, as well as by implementing other molecular biology techniques known in the art. Such probes and oligonucleotides typically comprise various regions of the sequence of SEQ ID NO:1 or 3, or encode various regions of the sequence of SEQ ID NO:2 or 4. Alternatively, additional target proteins for CM101 may be expression cloned. This method is described in WO 00/05375. Alternatively, subtractive hybridization between similar tissues that do and do not express the GBS toxin receptor may be used to isolate additional GBS toxin receptors. Examples of such tissues are wounded tissue and corresponding non-wounded tissue; tumor tissue and a sample of the same tissue that is free of histopathological abnormality; and lung tissue of appropriate mammals during expression of the GBS toxin receptor and shortly after expression stops. Upon discovery of an additional receptor, the probes may comprise various regions of the newly discovered receptor.

Polynucleotides useful for cloning genes encoding GBS toxin receptors of various organisms can be determined by comparing the amino acid sequences of homologous proteins. (see Table 5 which compares amino acids 41-536 of HP59 with amino acids 1-495 of SP55). For example, conserved regions can be targeted for the synthesis of oligonucleotides or degenerate oligonucleotides to be used as probes for hybridization or nucleic acid amplification, techniques discussed further below. Stringency can be varied to achieve selective hybridization conditions whereby nucleic acid sequences having less than 95% identity with respect to each other will hybridize. These conditions are known in the art and discussed herein. Generally, the nucleic acid sequence identity between HP59 or SP55 and a nucleic acid sequence of interest will be at least about 80%, and more typically with preferably increasing identities of at least about 85% and 90%.

Polynucleotides can be used as probes under high stringency wash conditions and with corresponding hybridization conditions, as known in the art. Small polynucleotides, for example, polynucleotides 200 bases or fewer in length, are often referred to in the art as oligonucleotides. Techniques for using polynucleotides as probes to detect the same or related nucleic acid sequences is well known in the art. See, for example, Sambrook et al, especially Chapter 11. Usually, probes can be made from polynucleotides that are 10 to 200 bases in length. Preferably probes are made from polynucleotides 10 to 60 nucleotides in length and most preferably 12 to 40 bases in length. Specific probes can be designed based on results obtained using nucleic acid homology computer programs such as FASTA, which uses the method of Pearson and Lipman (*Proc. Natl. Acad. Sci. USA* 85:2444-2448 (1988)) and shows the degree of identity between compared sequences. The size of the probe is dependent upon the region of the gene to which it will be hybridized. The size of the probe increases as the degree of homology to undesirable nucleic acid sequences increases. A probe 10-50 nucleotides in length can be used, preferably more than 50 nucleotides, even more preferably more than 100 nucleotides, and most preferably a probe made from the entire coding region of a GBS toxin receptor will be used. To decrease the number of false positives, preferably two probes are used to identify clones that bind to both probes under hybridization and wash conditions. Oligonucleotides can be synthesized on an Applied BioSystems oligonucleotide synthesizer according to specifications provided by the manufacturer.

Typically, hybridization and washing conditions are performed at according to conventional hybridization procedures. Typical hybridization conditions for screening plaque lifts (Benton and Davis (1978) *Science* 196: 180) can be: 50% formamide, 5×SSC (sodium chloride, sodium citrate) or SSPE (sodium chloride, sodium phosphate, EDTA), 1-5× Denhardt's solution, 0.1-1% SDS, 100-200 µg sheared heterologous DNA or tRNA, 0-10% dextran sulfate, $1 \times 10^5$ to $1 \times 10^7$ cpm/ml of denatured probe with a specific activity of about $1 \times 10^8$ cpm/µg, and incubation at 42° C. for about 6-36 hours. Prehybridization conditions are essentially identical except that probe is not included and incubation time is typically reduced. Washing conditions are typically 1-3×SSC, 0.1-1% SDS, 42-70° C. with change of wash solution at about 5-30 minutes. For high stringency hybridization conditions, various parameters can be altered to increase the stringency of hybridization, such as by increasing the temperature of incubation with the labeled probe. Preferably, for greater flexibility in experimental design, the probe can be hybridized at a lower temperature, such as, for example, room temperature and the stringency can then be modified by altering the salt concentration and temperature of the wash solutions. For high stringency a wash temperature of greater than or equal to 42° C. can be used, such as, for example, 68° C., in a wash buffer having a salt concentration less than 3×SSC, such as, for example, 0.1×SSC. In some cases, TMACL can also be used, particularly for polynucleotides rich in G-C base pairs in order to decrease non-specific binding. A lower stringency wash can be used to hybridize polynucleotides with lower identities or polynucleotides that are less than 60 base pairs in length. For a low stringency wash, temperatures of less than or equal to 42° can be used in a wash buffer having a salt concentration of greater than or equal to 2×SSC:

TABLE 5

Alignment of Human and Sheep GBS Toxin Receptor Amino Acid Sequences

```
SP55 MKSPVSDLAPSDGEEGSDRTPLLQRAPRAEPAPVCCSARYNLAFLSFFGF  50
     | ||| |||  ||||  ||||||  |||||  |||||||||||| | |||
HP59 MRSPVRDLARNDGEESTDRTPLLPGAPRAEAAPVCCSARYNLAILAFFGF  91

SP55 FVLYSLRVNLSVALVDMVDSNTTAKDNRTSYECAEHSAPIKVLHNQTGKK 100
     | |  |||||||||||||||||||  |||||  | |||||||| ||||||
HP59 FIVYALRVNLSVALVDMVDSNTTLEDNRTSKACPEHSAPIKVHHNQTGKK 141

SP55 YRWDAETQGWILGSFFYGYIITQIPGGYVASRSGGKLLLGFGIFATAIFT 150
     | ||||||||||||||||||||||||||||| | ||| ||||| ||  |
HP59 YQWDAETQGWILGSFFYGYIITQIPGGYVASKIGGKMLLGFGILGTAVLT 191

SP55 LFTPLAADFGVGALVALRALEGLGEGVTYPAMHAMWSSWAPPLERSKLLS 200
     |||| ||| ||| |  |||||||||||| |||||||||||||||||||||
HP59 LFTPIAADLGVGPLIVLRALEGLGEGVTFPAMHAMWSSWAPPLERSKLLS 241

SP55 ISYAGAQLGTVVSLPLSGVICYYMNWTYVFYFFGIVGIIWFILWICLVSD 250
     ||||||||||| ||||||| |||||||||||||||  || || ||| ||||
HP59 ISYAGAQLGTVISLPLSGIICYYMNWTYVFYFFGTIGIFWFLLWIWLVSD 291
```

TABLE 5-continued

Alignment of Human and Sheep GBS Toxin Receptor Amino Acid Sequences

```
SP55 TPETHKTITPYEKEYILSSLKNQLSSQKSVPWIPMLKSLPLWAIVVAHFS 300
     ||  || |  |||||||||| ||||||||||| | |||||||||||||||
HP59 TPQKHKRISHYEKEYILSSLRNQLSSQKSVPWVPILKSLPLWAIVVAHFS 341

SP55 YNWTFYTLLTLLPTYMKEVLRFNIQENGFLSAVPYLGCWLCMILSGQAAD 350
     |||||||||||||||||| |||| |||||||  |||| ||||||||||||
HP59 YNWTFYTLLTLLPTYMKEILRFNVQENGFLSSLPYLGSWLCMILSGQAAD 391

SP55 NLRARWNFSTLWVRRVFSLIGMIGPAIFLVAAGFIGCDYSLAVAFLTIST 400
     |||| |||||| ||| |||||||||| |||||||||||||||||||||||
HP59 NLRAKWNFSTLCVRRIFSLIGMIGPAVFLVAAGFIGCDYSLAVAFLTIST 441

SP55 TLGGFCSSGFSINHLDIAPSYAGILLGITNTFATIPGMIGPIIARSLTPE 450
     |||||||||||||||||||||||||||||||||||||| || || ||||
HP59 TLGGFCSSGFSINHLDIAPSYAGILLGITNTFATIPGMVGPVIAKSLTPD 491

SP55 NTIGEWQTVFCIAAAINVFGAIFFTLFAKGEVQNWAISDHQGHRN      495
     || ||||||| |||||||||||||||||||||||||  || |||
HP59 NTVGEWQTVFYIAAAINVFGAIFFTLFAKGEVQNWALNDHHGHRH      536
```

Vaccine Preparation

A preferred embodiment of the present invention is a conjugate vaccine in which the GBS toxin receptor or fragment thereof is covalently linked to a "carrier" protein or polypeptide. The linkage serves to increase the antigenicity of the GBS toxin receptor polypeptide. Methods for forming conjugate vaccines from an antigenic molecule and a "carrier" protein or polypeptide are known in the art (Jacob, C, O, et al., *Eur. J. Immunol.* 16:1057-1062 (1986); Parker, J. M. R. et al., In: Modern Approaches to Vaccines, Chanock, R. M. et al., eds, pp. 133-138, Cold Spring Harbor Laboratory, Cold Spring Harbor, N.Y. (1983); Zurawski, V. R, et al., *J. Immunol.* 121:122-129 (1978); Klipstein, F. A, et al., *Infect. Immun.* 37:550-557 (1982); Bessler, W. G, *Immunobiol.* 170:239-244 (1985); Posnett, D. N, et al., *J. Biol. Chem.* 263:1719-1725 (1988); Ghose, A. C, et al., *Molec. Immunol.* 25:223-230 (1988)). A prototype model for conjugate vaccines was developed against *Hemophilus influenzae* (Anderson, P, *Infec. and Immun.* 39:223-238 (1983); Chu, C, et al., *Infect. Immun.* 40:245-256 (1983); Lepow, M, *Pediat. Infect. Dis. J.* 6:804-807 (1987)), and this model may be employed in constructing the novel vaccines of the present invention. Additional methods for producing such a conjugate vaccine are disclosed by Anderson, P. W, et al., European Patent Publication 245,045; Anderson, P. W, et al., U.S. Pat. Nos. 4,673,574 and 4,761,283; Frank, R. et al., U.S. Pat. No. 4,789,735; European Patent Publication No. 206,852; Gordon, L. K, U.S. Pat. No. 4,619,828; and Beachey, E. H, U.S. Pat. No. 4,284,537. Useful carriers include keyhole limpet hemocyanin (KLH), bovine serum albumin (BSA), ovalbumin, human serum albumin, human gamma globulin, chicken immunoglobulin G, bovine gamma globulin and tetanus toxoid. Alternatively, the GBS toxin polypeptide may be conjugated or linked to immunogenic polysaccharides such as group A *Streptococci* polysaccharide, C-polysaccharide from group B *Streptococci*, or the capsular polysaccharide of *Streptococci pnuemoniae.*

Another embodiment of the present invention is a whole cell vaccine in which the transfected or normal cell expressing a GBS toxin receptor on its membrane may be alive or fixed and killed.

As would be understood by one of ordinary skill in the art, when the vaccine of the present invention is provided to an individual, it may be in a composition which may contain salts, buffers, adjuvants, or other substances which are desirable for improving the efficacy of the composition. Normally, the adjuvant and the composition are mixed prior to presentation to the immune system, or presented separately, but into the same site of the mammal being immunized. Alum is a registered adjuvant for human use. Other adjuvants are being developed for human use and it is anticipated that these other adjuvants would be suitable for use in preparing compositions for human vaccination in accordance with this invention. Suitable adjuvants for the vaccination of animals include but are not limited to oil emulsions such a Freund's complete or incomplete adjuvant (not suitable for livestock use), Marcol 52: Montanide 888 (Marcol is a Trademark of Exxon. Montanide is a Trademark of SEPPIC, Paris), squalane or squalene, Adjuvant 65 (containing peanut oil, mannide monooleate and aluminium monostearate), mineral gels such as aluminium hydroxide, aluminium phosphate, calcium phosphate and alum, surfactants such a hexadecylamine, octadecylamine, lysolecithin, dimethyldioctadecylammonium bromide, N,N-dioctadecyl-N',N'-bis(2-hydroxyethyl) propanediamine, methoxyhexadecylglycerol and pluronic polyols, polyanions such as pyran, dextran sulfate, polyacrylic acid and carbopol, peptides and amino acids such as muramyl dipeptide, dimethylglycine, tuftsin and trehalose dimycolate.

The polypeptides of the present invention can also be administered following incorporation into liposomes or other micro-carriers.

Pharmaceutical Compositions

Pharmaceutical compositions of the invention preferably include a pharmaceutically acceptable carrier that may contain a variety of components that provide a variety of functions, including regulation of drug concentration, regulation of solubility, chemical stabilization, regulation of viscosity, absorption enhancement, regulation of pH, and the like. For example, in water soluble formulations the pharmaceutical composition preferably includes a buffer such as a phosphate buffer, or other organic acid salt, preferably at a pH of between about 7 and 8. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g. Remington's Pharmaceutical Science, $19^{th}$ edition (Mack Publishing Company, Easton, Pa.).

For purposes of parenteral administration, solutions in sesame or peanut oil or in aqueous propylene glycol can be employed, as well as sterile aqueous solutions of the corresponding water-soluble, alkali metal or alkaline-earth metal salts previously enumerated.

Such aqueous solutions should be suitably buffered, if necessary, and the liquid diluent first rendered isotonic with sufficient saline or glucose. Solutions of the GBS toxin receptor polypeptide as a free base or a pharmacologically acceptable salt can be prepared in water suitably mixed with a surfactant such as hydroxypropylcellulose. A dispersion can also be prepared in glycerol, liquid polyethylene glycols and mixtures thereof and in oils. Under ordinary conditions of storage and use, these preparations contain a preservative to prevent the growth of microorganisms. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the GBS toxin receptor polypeptide in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

Administration

Route

The polypeptides, compositions and vaccines of the present invention can be administered orally, parenterally by injection, rapid infusion, nasopharyngeal absorption (intranasopharangeally), dermoabsorption, or rectally. They may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, and the like.

Dosage and Frequency of Administration

The amount of GBS toxin receptor polypeptide to be combined with carrier, diluent, excipient and/or adjuvant to produce a single pharmaceutical composition or vaccine dosage form will vary depending upon the pathoangiogenic condition being vaccinated against, the mammal's propensity for developing such condition or the severity of such condition, the mammal to be treated and the particular time and route of administration. It will be understood, also, that the specific dose level for any particular mammal will depend upon a variety of factors including the age, body, weight, general health, sex, and diet of such mammal. Effective dosages can be readily established by one of ordinary skill in the art through routine trials establishing dose-response curves.

Many different techniques exist for the timing of the immunizations when a multiple administration regimen is utilized. It is possible to use the compositions of the invention more than once to increase the level, diversity and stability of the immune response in the immunized animal. Multiple doses may be required to maintain a state of immunity to GBS toxin receptor. If so, multiple immunizations will be given at intervals appropriate to maintain the desired immune response.

Monitoring Immune Response

It is desirable to characterize the immune response of a mammal that has received a vaccine according to the method of the present invention. Such characterization is preferably made in light of the mammal's immune response to the GBS toxin receptor and to various other standards prior to the initial administration of the receptor. Subsequent testing is performed within a reasonable period, preferably at least six weeks, after administration of the GBS toxin receptor. Such testing may be performed again at regular intervals thereafter or on an as-needed basis, depending on the mammal's condition. For instance, at the desired timepoint, a blood sample is harvested from the mammal and preserved in an appropriate manner until testing can be carried out. Preservation methods of the blood samples include separation of blood sera from other blood components, cooling or freezing, and preservation with various buffering or anti-coagulatory agents. Testing may also be performed on urine, stool, and tissue from lung, lymph nodes, spleen, bond marrow, ulcers, skin lesions and exudate and other tissues affected by the pathoangiogenic condition being tested.

The presence of antibodies in the serum (i.e. a humoral immune response to the GBS toxin receptor) may be determined by ELISA, RAST, EIA, hemagglutination inhibition, other radioimmunoassay techniques, and latex agglutination methods and by general serological assays including white blood cell counts, measurement of total and differentiated immunoglobulin levels, including IgM, total IgG, $IgG_1$, $IgG_2$, $IgG_3$ and $IgG_4$, or other methods known to one of skill in the art. One possible method for performing an ELISA determination involves plating the GBS toxin receptor of interest onto ELISA plates. After unbound antigen is washed off the plates, excess protein reactive sites on the plates are blocked with a blocking buffer. Following removal of the blocking buffer, a dilution series of sera in PBS is added into wells of the blocked ELISA plates and incubated for one hour at 37° C. After removal of the dilution series, the plates are washed and a conjugated antibody solution in PBS (antibody is against the vaccinated species) is added to the wells of the ELISA plate, which is then incubated for one hour at 37° C. After removal of the conjugated antibody solution, the plates are washed and the appropriate chromogenic substrate is added to the wells to allow for color development. After a 30-minute incubation, color development is stopped and the absorbance readings of the wells are read on a spectrophotometer. The absorbance readings for each group at each dilution are averaged and plotted versus the reciprocal dilution. Positive and negative controls are an important part of this determination as is a comparison with the pre-immunization (baseline) testing. If antibodies can be detected at a dilution of about 1:200 or more, then the mammal has a positive immune response.

Determination of a cellular immune response may be made by methods known to those of skill in the art, including those discussed herein. The presence of T cells that recognize the GBS toxin receptor can be tested by administering a sample of the GBS toxin receptor subcutaneously and examining the skin of the mammal (preferably human) 72 hours later to see if the skin at the site of administration is raised by about 1 mm or more. The size of such wheals are typically measured and can be correlated to the degree of immune response. Such a response is a positive immune response. Alternatively, a cellular immune response can be determined by such methods as measuring C-reactive protein serum levels, complement levels, including normal complement and C-3 detection, erythrocyte sedimentation rate, haptoglobin serum levels, immunoprotein levels and other protein serum levels.

A positive immune response means that the pathoangiogenic condition is prevented or attenuated. Prevention and attenuation can be demonstrated by methods known in the art, including but not limited to those discussed herein.

One method of demonstrating prevention is to administer the vaccine to or practice the method upon a group of individuals from a population that is susceptible to the pathoangiogenic condition of interest and compare the incidence of the condition in such group with the incidence of the condition in the rest of the population that did not receive the vaccine or method. For example, humans who smoke are susceptible to lung cancer. A group from a test population of statistically matched smokers who do not have lung cancer can be given a vaccine or method of the present invention while the remainder of the test population will not receive any treatment. Both groups are monitored for lung cancer. If no members of the group that received the vaccine or method have developed lung cancer by a time when a statistically significant number of the remainder of the test population have developed the disease, then the vaccine or method can be concluded to prevent lung cancer. If cases of lung cancer develop in the treated group but do so at a statistically significant lower rate than that of the remainder of the population, the vaccine or method can be concluded to decrease the incidence of lung cancer. One of skill in the art can demonstrate prevention of other pathoangiogenic conditions by similar methods known in the art including testing of populations that are susceptible to the particular disease on account of genetic and/or environmental factors.

Support for additional aspects of the present invention and methods for making and using the invention are published in WO 00/05375.

EXAMPLES

Example 1

Immunization with a Mixture of Three Fragments from Human GBS Toxin Receptor Retards Tumor Growth Peptides Hab1, Hab2 and Hab3, which are shown in Table 3, are fragments from amino terminus of HP59 that were selected as immunogens based on hydrophilicity. They were synthesized in vitro (Sigma-Genosis, The Woodlands, Tex.) and conjugated to keyhole limpet hemocyanin (KLH), a glycoprotein which served as an adjuvant. Experimental C57 mice (n=8, four males and four females) were immunized by subcutaneous injection of 100 micrograms of a mixture of the three peptide conjugates in complete Freund's adjuvant (CFA). Two weeks, four weeks and six weeks later, each of these mice received a subcutaneous injection of 100 micrograms of this mixture in incomplete Freund's adjuvant (IFA). A final injection of 100 micrograms of this mixture in IFA was given intradermally at eight weeks. Control C57 mice (n=8) were immunized at the same times in the same manner with only KLH and Freund's adjuvant.

Experimental mice were bled from the tail vein 6 weeks after the initial immunization and every four weeks thereafter and the level of antibodies formed to the HP59 derived peptides were established by ELISA. When a positive antibody titer was obtained from all experimental mice, both control and experimental mice were challenged with tumor cells as follows: 50,000 mouse melanoma B1-6 cells or Lewis lung tumor cells were suspended in 0.6% agar and injected subdermally. The volume of the tumors was measured 6, 8, 10, 12 and 14 days after the tumor cell injections. As shown in Table 6, the melanoma tumors of immunized mice were 45% smaller than those of their control counterparts and the Lewis lung tumors of immunized mice were 38% smaller than those of their control counterparts. The results of both experiments were statistically significant. For the melanoma experiments, the paired t test for treated versus control was t=2.3898 with five degrees of freedom and the one tailed p=0.0312, which is considered significant. For the Lewis lung experiments, the paired t test for treated versus control was t=2.9899 with five degrees of freedom and the one tailed p=0.0152, which is considered significant.

TABLE 6

| Tumor progression (volume = # × mm³) | | | | | |
|---|---|---|---|---|---|
| Tumor Type | Day 6 | Day 8 | Day 10 | Day 12 | Day 14 |
| Melanoma (n = 4) | 15.6 | 83.3 | 131.3 | 350.1 | 429.8 |
| Control (n = 4) | 20.4 | 118.2 | 174.5 | 518.6 | 783.5 |
| Lewis Lung (n = 4) | | 36.9 | 70.8 | 144.8 | 194.6 |
| Control (n = 4) | | 68.8 | 119.4 | 178.8 | 315.1 |

Example 2

Treatment of Immunized Mammals with CM101

Mice immunized and challenged with tumor cells as described in Example 1 may additionally receive weekly intravenous infusions of 60 μg/kg of the GBS toxin CM101 (CarboMed, Inc., Brentwood, Tenn.) or mock injections. Tumor progression is compared in the CM101-treated and control mice and the degree of tumor growth retardation or elimination is calculated using standard statistical methods. Additional experiments at different dose levels are conducted to determine a dose-response relationship.

Example 3

Treatment of Immunized Mammals with Immunocompatible Antibodies

Mice immunized and challenged with tumor cells as described in Example 1 may additionally receive weekly injections of 100 μg of a mixture of mouse monoclonal antibodies specific for HP59 or mock injections. Such antibodies are obtained by immunizing mice with 100 mg of the synthetic peptides shown in Table 3 in accordance with the methods taught in Harlow et al., ANTIBODIES: A LABORATORY MANUAL, Cold Spring Harbor Press, pp. 139-240 (1989). Tumor progression is compared in the antibody-treated and control mice and the degree of tumor growth retardation or elimination is calculated using standard statistical methods. Additional experiments at different dose levels are conducted to determine a dose-response relationship.

Example 4

Treatment of Immunized Mammals with Autologous T Cells

T cells may be removed from mice immunized and challenged with tumor cells as described in Example 1 and either incubated with a mixture of the Hab1, Hab2 and Hab3 peptides or mock incubated for 72 hours. The T cells are returned to each donor mouse by intravenous injection. Tumor progression is compared in the peptide-incubated and control mice and the degree of tumor growth retardation or elimination is calculated using standard statistical methods. Additional experiments at different dose levels are conducted to determine a dose-response relationship.

Example 5

Immunization with a Mixture Five Fragments from Human and Sheep GBS Toxin Receptors Retards Tumor Growth Two groups of male and female C57 mice and equal size controls were immunized with a mixture of five peptides shown in Tables 3 and 4, p56a, p55a, p57a, Hab1, and Hab2. These peptides were derived from the homologous proteins HP59 and SP55 (87%), conjugated with keyhole limpet hemocyanin (KLH) (Sigma Genosys, TX) and emulsified in complete Freund's Adjuvant (CFA), by intradermal injection in three places at the base of the tail.

The first immunization was followed two weeks and four weeks later with repeat intradermal injections of antigen KLH conjugate and incomplete Freund's Adjuvant (IFA) for the experimental group. IFA alone was given to control animals. Animals were bled after 5 weeks and shown to have antibody titer of 1:200 with optical density (O.D.) of >2.0. to one extracellular peptide based on a seven transmembrane domain (7TMD) configuration.

Lewis Lung cell suspension ($5 \times 10^4$ cells) in 3% agar was implanted subcutaneously in seven immunized male and five immunized females. Four male and four female CFA and IFA immunized mice served as controls. The mice were observed until the control tumors began to ulcerate at which time mice were sacrificed and tissues, including tumors, were collected.

The growth curve for the Lewis Lung tumors in C57 mice are shown in FIG. 1. The y-axis represents tumor volume and the x-axis represents the day the tumor volume was measured. Male controls are denoted by blackened diamonds, female controls are denoted by blackened circles; male immunized are denoted by clear circles and female immunized are denoted by clear diamonds. The raw data of tumor volumes from different days were recorded. A paired t-test using tumor volumes at the five last measurements shows a significant difference (p=0.025) in the average tumor volumes for the non-immunized male and female with the average for the immunized groups. The overall tumor burden in the immunized mice was only 38.3% of the control.

Example 6

Retardation of Melanomas in Female Mammals

Five each of HP59/CFA and CFA immunized, female C57 mice were inoculated intravenously with 1,000 melanoma cells. Time to death was the endpoint. Mice were to be sacrificed when respiratory distress was obvious.

Figure 2:
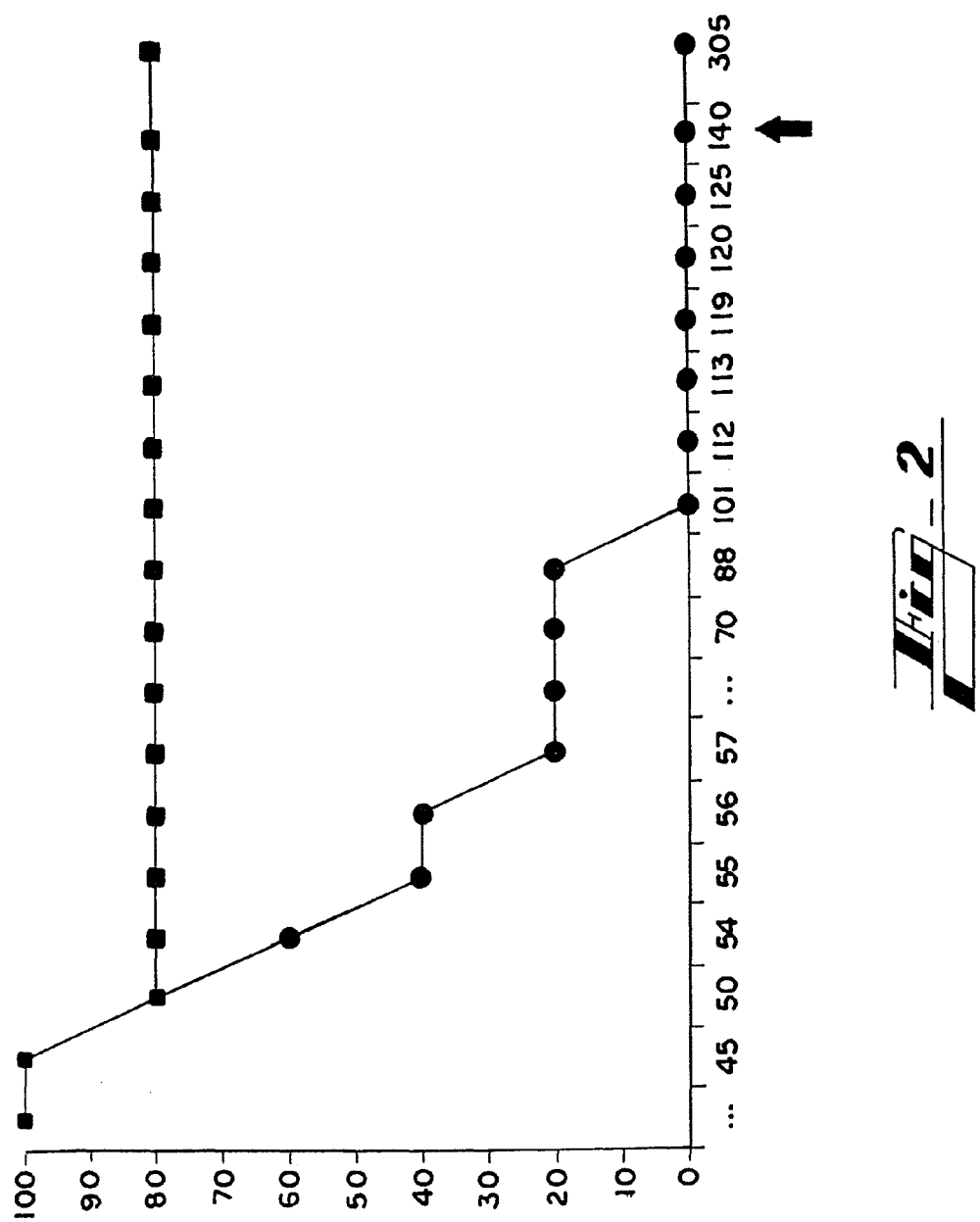
FIG. 2 presents survival curves for female mammals immunized with a composition of the present invention and challenged intravenously with melanoma cells and for female control mammals equally challenged but not immunized. The y-axis represents percentage of survivors and the x-axis represents the number of days of survival. The blackened circles denote female controls and the blackened squares denote female immunized mammals.

The five female controls died on days 46, 52, 54, 62 and 100. The autopsy of the diseased control mice showed lungs to be infiltrated by numerous metastasis. One immunized female died early with no sign of tumors. The remaining four immunized mice were all alive at day 140 with no signs of disease, at which time two of them were inoculated with an additional 1,000 melanoma cells (denoted by an arrow in FIG. 2). The remaining four immunized mice continued to show no signs of disease on day 305. FIG. 2 shows survival curves for the female mice challenged intravenously with 1000 melanoma cells. The y-axis represents percentage of survivors and the x-axis represents the number of days of survival. The blackened circles denote female controls and the blackened squares denote female immunized mammals.

All publications, patents and patent applications mentioned in this specification are herein incorporated by reference to the same extent as if each individual publication, patents or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of attenuating a pathoangiogenic condition in a mammal, comprising administering to the mammal a composition comprising a polypeptide in an amount effective to induce or maintain an immune response to the Group B β-hemolitic *streptococci* (GBS) toxin receptor in the mammal, the immune response attenuating the pathoangiogenic condition,
   wherein the polypeptide comprises a mammalian GBS toxin receptor or is an immunogenic fragment of the GBS toxin receptor,
   wherein the GBS toxin receptor is capable of binding to GBS toxin CM101,
   wherein the pathoangiogenic condition is tumor growth,
   wherein the polypeptide is encoded by a nucleic acid sequence having greater than 95% sequence identity to SEQ ID NO:1, and
   wherein the fragment of the mammalian GBS toxin receptor has at least nine amino acids.

2. The method of claim 1, wherein the GBS toxin receptor has 100% identity to SEQ ID NO:2.

3. The method of claim 1, wherein the polypeptide comprises SEQ ID NO:2.

4. The method of claim 1, wherein the polypeptide is the immunogenic fragment of the GBS toxin receptor and is 10-50 amino acids in length.

5. A method of attenuating a pathoangiogenic condition in a mammal, comprising administering to the mammal a composition comprising a polypeptide, in an amount effective to induce or maintain an immune response to the Group B β-hemolitic *streptococci* (GBS) toxin receptor in the mammal, the immune response attenuating the pathoangiogenic condition,
   wherein the polypeptide comprises a mammalian GBS toxin receptor or is an immunogenic fragment of the GBS toxin receptor,
   wherein the pathoangiogenic condition is tumor growth,
   wherein the fragment of the mammalian GBS toxin receptor has at least nine amino acids,
   wherein the GBS toxin receptor is capable of binding to GBS toxin CM101, and
   wherein the GBS toxin receptor has at least about 86% identity to SEQ ID NO:2.

6. The method of claim 5, wherein the polypeptide is the immunogenic fragment of the GBS toxin receptor and is 10-50 amino acids in length.

7. A method of attenuating a pathoangiogenic condition in a mammal, comprising administering to the mammal a composition comprising a polypeptide comprising an amino acid sequence that has at least about 86% identity to SEQ ID NO:2, wherein the polypeptide is capable of binding the Group B β-hemolitic *streptococci* (GBS) toxin CM101, and wherein the pathoangiogenic condition is tumor growth.

8. The method of claim 7, wherein the amino acid sequence of said isolated polypeptide differs from the amino acid sequence selected from SEQ ID NO:2 at no more than about 1% of the amino acid residues.

9. The method of claim 7, wherein the amino acid sequence of the polypeptide differs from SEQ ID NO:2 by one amino acid residue.

10. The method of claim 7, wherein the different amino acid residues are conservative substitutions of the corresponding residues of SEQ ID NO:2.

* * * * *